US012714352B2

(12) United States Patent
Xie et al.

(10) Patent No.: US 12,714,352 B2
(45) Date of Patent: Aug. 25, 2026

(54) MULTI-LEAD ELECTROCARDIOGRAM DETECTION METHOD AND ELECTRONIC DEVICE

(71) Applicant: Honor Device Co., Ltd., Shenzhen (CN)

(72) Inventors: Zhibo Xie, Shenzhen (CN); Jingbo Zou, Shenzhen (CN); Yinjiong Tan, Shenzhen (CN); Haitong Zhang, Shenzhen (CN)

(73) Assignee: HONOR DEVICE CO., LTD., Shenzhen (CN)

( * ) Notice: Subject to any disclaimer, the term of this patent is extended or adjusted under 35 U.S.C. 154(b) by 178 days.

(21) Appl. No.: 18/838,005

(22) PCT Filed: Aug. 23, 2023

(86) PCT No.: PCT/CN2023/114378
§ 371 (c)(1),
(2) Date: Aug. 13, 2024

(87) PCT Pub. No.: WO2024/051494
PCT Pub. Date: Mar. 14, 2024

(65) Prior Publication Data

US 2025/0160719 A1 May 22, 2025

(30) Foreign Application Priority Data

Sep. 5, 2022 (CN) ........................ 202211078466.4

(51) Int. Cl.
*A61B 5/318* (2021.01)
*A61B 5/00* (2006.01)
*A61B 5/339* (2021.01)

(52) U.S. Cl.
CPC ............. *A61B 5/318* (2021.01); *A61B 5/339* (2021.01); *A61B 5/681* (2013.01); *A61B 2562/222* (2013.01)

(58) Field of Classification Search
CPC ... A61B 2562/222; A61B 5/318; A61B 5/327; A61B 5/332; A61B 5/339; A61B 5/681; A61B 5/684
See application file for complete search history.

(56) References Cited

U.S. PATENT DOCUMENTS 5,339,823 A 8/1994 Reinhold, Jr.
2002/0087088 A1 7/2002 Brodnick
(Continued)

FOREIGN PATENT DOCUMENTS

CN 103494606 A 1/2014
CN 104510462 A 4/2015
(Continued)

*Primary Examiner* — Michael T Rozanski
(74) *Attorney, Agent, or Firm* — Conley Rose, P.C.

(57) ABSTRACT

A multi-lead electrocardiogram detection method and an electronic device. The method includes: obtaining potential signals of surfaces of two upper limbs and a lower limb of a human body and six equivalent positions on a chest of the human body in response to a user operation, and determining electrocardiogram signals corresponding to twelve leads based on the potential signals. The user operation is an operation that first and second detection electrodes are in contact with the two upper limbs of the human body, and the third detection electrode is in contact with the lower limb of the human body and the six equivalent positions on the chest in sequence.

20 Claims, 13 Drawing Sheets

(56) References Cited

U.S. PATENT DOCUMENTS

| | | | |
|---|---|---|---|
| 2014/0194760 | A1 | 7/2014 | Albert |
| 2014/0228665 | A1 | 8/2014 | Albert et al. |
| 2015/0099957 | A1 | 4/2015 | Kuo et al. |
| 2016/0287172 | A1 | 10/2016 | Morris et al. |
| 2021/0169392 | A1 | 6/2021 | Albert et al. |
| 2021/0267525 | A1 | 9/2021 | Albert |
| 2023/0363684 | A1 | 11/2023 | Ugander et al. |

FOREIGN PATENT DOCUMENTS

| | | | |
|---|---|---|---|
| CN | 107427235 | A | 12/2017 |
| CN | 109893122 | A | 6/2019 |
| CN | 110115580 | A | 8/2019 |
| CN | 113384278 | A | 9/2021 |
| CN | 115886831 | A | 4/2023 |
| TW | 201016190 | A | 5/2010 |
| TW | M551476 | U | 11/2017 |
| WO | 2014172451 | A1 | 10/2014 |
| WO | 2022063975 | A1 | 3/2022 |

MULTI-LEAD ELECTROCARDIOGRAM DETECTION METHOD AND ELECTRONIC DEVICE

CROSS-REFERENCE TO RELATED APPLICATIONS

This is a U.S. National Stage of International Application No. PCT/CN2023/114378 filed on Aug. 23, 2023, which claims priority to Chinese Patent Application No. 202211078466.4, filed with the China National Intellectual Property Administration on Sep. 5, 2022, both of which are incorporated herein by reference in their entireties.

TECHNICAL FIELD

This application relates to the field of intelligent terminal technologies, and in particular, to a multi-lead electrocardiogram detection method and an electronic device.

BACKGROUND

With rapid development of electronic technologies and people's increasing attention to their own health status, portable devices are increasingly widely used to assist in health assessment. For example, an electrocardiogram (Electronic diagram, ECG) detection function is integrated into some bands in a conventional technology to detect a cardiac function of a user. A first electrode is disposed on the bottom surface of a watch body of a band, and a second electrode is disposed on the front surface of the watch body. In a detection status, the first electrode is in contact with a wrist wearing the band, and the second electrode is in contact the other wrist, so that an electrocardiogram signal corresponding to a lead I (a single lead) between both hands can be obtained.

The ECG detection function of existing portable devices mainly relates to single-lead ECG detection, and single-lead ECG detection can only detect time series anomalies (such as atrial fibrillation and a premature beat) of the electrocardiogram signals, but cannot effectively detect scenarios, such as acute myocardial infarction, that need to be detected by using a multi-lead ECG.

Onset of acute myocardial infarction is generally urgent. Therefore, how to implement a multi-lead ECG detection function through portable devices to improve timeliness of detection of diseases such as acute myocardial infarction is an urgent problem to be resolved.

SUMMARY

To resolve the foregoing technical problem, this application provides a multi-lead electrocardiogram detection method and an electronic device. Twelve-lead ECG measurement may be implemented by using three detection electrodes. Not only time series anomalies (such as atrial fibrillation and a premature beat) of electrocardiogram signals may be detected, but scenarios, such as acute myocardial infarction, that need to be detected by using a multi-lead ECG can also be effectively detected in a timely manner.

According to a first aspect, an embodiment of this application provides a multi-lead electrocardiogram detection method, applied to an electronic device. The electronic device includes a first detection electrode, a second detection electrode, and a third detection electrode that are configured to collect electrical signals on a surface of a human body. The multi-lead electrocardiogram detection method includes: obtaining potential signals of surfaces of two upper limbs and a lower limb of the human body in response to a first operation, where the first operation is an operation that the first detection electrode is in contact with one upper limb of the human body, the second detection electrode is in contact with the other upper limb of the human body, and the third detection electrode is in contact with the lower limb of the human body; obtaining, in sequence, potential signals of surfaces of six equivalent positions on a chest of the human body in response to a second operation, where the second operation is an operation that the third detection electrode is in contact with the six equivalent positions on the chest of the human body in sequence, the six equivalent positions on the chest are six positions obtained after six preset positions on the chest respectively move in directions of the two upper limbs by a preset distance, and the preset distance is a distance between a first center point determined when the first detection electrode is in contact with one upper limb of the human body, the second detection electrode is in contact with the other upper limb of the human body, and the third detection electrode is in contact with the lower limb of the human body and a second center point determined when the first detection electrode is in contact with one upper limb of the human body, and the second detection electrode is in contact with the other upper limb of the human body; and determining electrocardiogram signals corresponding to twelve leads based on the potential signals of the surfaces of the two upper limbs and the lower limb of the human body and the potential signals of the surfaces of the six equivalent positions on the chest of the human body.

Two of the three electrodes are in contact with the two upper limbs of a user, and the other electrode touches a lower limb position and the six equivalent positions on the chest in sequence and collects a potential signal at each position. The electronic device may obtain electrocardiogram signals corresponding to six limb leads based on the collected potential signals of the two upper limbs and the lower limb of the human body, and the electronic device may obtain electrocardiogram signals corresponding to six chest leads based on collected electrical signals of the two upper limbs of the human body and the six equivalent positions on the chest. This is because vector directions in which the second center point determined when the first detection electrode is in contact with one upper limb of the human body, and the second detection electrode is in contact with the other upper limb of the human body points to the six equivalent positions on the chest are in a one-to-one correspondence with vector directions in which the first center point determined when the first detection electrode is in contact with one upper limb of the human body, the second detection electrode is in contact with the other upper limb of the human body, and the third detection electrode is in contact with the lower limb of the human body points to the six preset positions on the chest. Therefore, in this scenario, leads at the six equivalent positions on the chest may be considered as equivalent leads of leads at the six preset positions on the chest, so that detection of equivalent leads of chest leads V1, V2, V3, V4, V5, and V6 is implemented, to obtain the electrocardiogram signals corresponding to the six chest leads. In conclusion, twelve-lead ECG measurement may be implemented by using the three electrodes. Scenarios, such as acute myocardial infarction, that need to be detected by using the multi-lead ECG may be effectively detected in a timely manner, and a structure is simple.

For example, the six preset positions include a first preset position, a second preset position, a third preset position, a fourth preset position, a fifth preset position, and a sixth preset position. The first preset position is the fourth intercostal space to the right of the sternum, the second preset position is the fourth intercostal space to the left of the sternum, the third preset position is located at a midpoint of a connection line between the second preset position and the fourth preset position, the fourth preset position is an intersection of the left midclavicular line and the fifth intercostal space, the fifth preset position is a position that is on the left anterior axillary line and that is at a same horizontal level as the fourth preset position, and the sixth preset position is a position that is on the left midclavicular line and that is at the same horizontal level as the fourth preset position.

For example, the six equivalent positions include a first equivalent position, a second equivalent position, a third equivalent position, a fourth equivalent position, a fifth equivalent position, and a sixth equivalent position. For example, the first equivalent position may be the second intercostal space to the right of the sternum, the second equivalent position is the second intercostal space to the left of the sternum, the third equivalent position is located at a midpoint of a connection line between the second equivalent position and the fourth equivalent position, the fourth equivalent position is an intersection of the left midclavicular line and the third intercostal space, the fifth equivalent position is a position that is on the left anterior axillary line and that is at the same horizontal level as the fourth preset position, and the sixth equivalent position is a position that is on the left midclavicular line and that is at the same horizontal level as the fourth preset position.

For example, the two upper limbs include an upper left limb (for example, a left hand) and an upper right limb (for example, a right hand), and the lower limb includes an abdomen and a food (a left food or a right food).

According to the first aspect, the multi-lead electrocardiogram detection method further includes: processing the obtained potential signals of the surfaces of the two upper limbs and the lower limb of the human body to determine the electrocardiogram signals corresponding to the six limb leads.

In some use scenarios, the electronic device (for example, a smartwatch) may perform processing, analysis, and the like on the obtained potential signals of the surfaces of the two upper limbs and the lower limb of the human body to determine the electrocardiogram signals corresponding to the six limb leads; or the electronic device may send the obtained potential signals to another electronic device (for example, a mobile phone), the potential signals of the surfaces of the two upper limbs and the lower limb of the human body are processed and analyzed through the another electronic device to determine the electrocardiogram signals corresponding to the six limb leads, and the determined electrocardiogram signals corresponding to the six limb leads are sent back to the electronic device (for example, the smartwatch).

According to the first aspect or any implementation of the first aspect, the two upper limbs include the upper left limb and the upper right limb. Processing the obtained potential signals of the surfaces of the two upper limbs and the lower limb of the human body to determine the electrocardiogram signals corresponding to the six limb leads includes: determining an electrocardiogram signal corresponding to a lead I based on a potential difference between a potential signal of a surface of the upper left limb and a potential signal of a surface of the upper right limb; determining an electrocardiogram signal corresponding to a lead II based on a potential difference between a potential signal of a surface of the lower limb and the potential signal of the surface of the upper right limb; determining an electrocardiogram signal corresponding to a lead III based on a potential difference between the potential signal of the surface of the lower limb and the potential signal of the surface of the upper left limb; and determining a potential of the first center point, and determining an electrocardiogram signal corresponding to a lead aVR, an electrocardiogram signal corresponding to a lead aVL, and an electrocardiogram signal corresponding to a lead aVF based on a potential difference between the potential of the first center point and the potential signal of the surface of the upper left limb, a potential difference between the potential of the first center point and the potential signal of the surface of the upper right limb, and a potential difference between the potential of the first center point and the potential signal of the surface of the lower limb.

According to the first aspect or any implementation of the first aspect, the multi-lead electrocardiogram detection method further includes: processing the obtained potential signals of the surfaces of the two upper limbs of the human body and the six equivalent positions on the chest of the human body to obtain the electrocardiogram signals corresponding to the six chest leads.

In some use scenarios, the electronic device (for example, the smartwatch) may perform processing, analysis, and the like on the obtained potential signals of the surfaces of the two upper limbs of the human body and the six equivalent positions on the chest of the human body to determine the electrocardiogram signals corresponding to the six chest leads; or the electronic device may send the obtained potential signals to the another electronic device (for example, the mobile phone), the potential signals of the surfaces of the two upper limbs of the human body and the six equivalent positions on the chest of the human body are processed and analyzed through the another electronic device to determine the electrocardiogram signals corresponding to the six chest leads, and the determined electrocardiogram signals corresponding to the six chest leads are sent back to the electronic device (for example, the smartwatch).

According to the first aspect or any implementation of the first aspect, processing the obtained potential signals of the surfaces of the two upper limbs of the human body and the six equivalent positions on the chest of the human body to obtain the electrocardiogram signals corresponding to the six chest leads includes: determining a potential of the second center point, and determining an electrocardiogram signal corresponding to a lead V1, an electrocardiogram signal corresponding to a lead V2, an electrocardiogram signal corresponding to a lead V3, an electrocardiogram signal corresponding to a lead V4, an electrocardiogram signal corresponding to a lead V5, and an electrocardiogram signal corresponding to a lead V6 based on a potential difference between the potential of the second center point and a potential signal of a surface of each of the six equivalent positions on the chest of the human body.

According to the first aspect or any implementation of the first aspect, before the obtaining, in sequence, potential signals of surfaces of six equivalent positions on a chest of the human body in response to a second operation, the method further includes: displaying a first interface, where the first interface includes a first information prompt box, and the first information prompt box is used to prompt the six equivalent positions on the chest. The user may place the third detection electrode based on a prompt, to complete detection, improve user experience, and improve accuracy of detection.

According to the first aspect or any implementation of the first aspect, before the obtaining, in sequence, potential signals of surfaces of six equivalent positions on a chest of the human body in response to a second operation, the method further includes: obtaining a preview image that is of an upper body of the human body and that is captured by a camera; and determining target objects in the preview image in sequence, where the target objects include the six equivalent positions on the chest of the human body. The user may place the third detection electrode based on the target objects, to complete detection, improve user experience, and improve accuracy of detection.

According to the first aspect or any implementation of the first aspect, the multi-lead electrocardiogram detection method further includes: outputting health status reminding information when the electrocardiogram signals corresponding to the twelve leads do not match preset electrocardiogram signals corresponding to the twelve leads, to notify the user of a health issue in a timely manner (for example, a risk of onset of acute myocardial infarction exists).

For example, the health status reminding information is output when an electrocardiogram signal corresponding to at least one lead in the electrocardiogram signals corresponding to the twelve leads has a typical disease-related feature (such as ST segment elevation and a pathologic Q wave) compared with a normal electrocardiogram signal.

For example, the health status reminding information may be output when one of the electrocardiogram signals corresponding to the twelve leads does not match a corresponding preset electrocardiogram signal, for example, has the typical disease-related feature compared with the normal electrocardiogram signal, or the health status reminding information may be output when a plurality of electrocardiogram signals in the electrocardiogram signals corresponding to the twelve leads do not match corresponding preset electrocardiogram signals, for example, have the typical disease-related feature compared with the normal electrocardiogram signal, or the like.

For example, the health status reminding information includes a statement and/or an alarm, a notification to a family member, or the like.

According to a second aspect, an embodiment of this application provides an electronic device. The electronic device includes a first detection electrode, a second detection electrode, and a third detection electrode that are configured to collect electrical signals on a surface of a human body. The electronic device further includes one or more processors, a memory, and one or more computer programs. The one or more computer programs are stored in the memory. When the computer program is executed by the one or more processors, the electronic device is enabled to perform the following steps: obtaining potential signals of surfaces of two upper limbs and a lower limb of the human body in response to a first operation, where the first operation is an operation that the first detection electrode is in contact with one upper limb of the human body, the second detection electrode is in contact with the other upper limb of the human body, and the third detection electrode is in contact with the lower limb of the human body; obtaining, in sequence, potential signals of surfaces of six equivalent positions on a chest of the human body in response to a second operation, where the second operation is an operation that the third detection electrode is in contact with the six equivalent positions on the chest of the human body in sequence, the six equivalent positions on the chest are six positions obtained after six preset positions on the chest respectively move in directions of the two upper limbs by a preset distance, and the preset distance is a distance between a first center point determined when the first detection electrode is in contact with one upper limb of the human body, the second detection electrode is in contact with the other upper limb of the human body, and the third detection electrode is in contact with the lower limb of the human body and a second center point determined when the first detection electrode is in contact with one upper limb of the human body, and the second detection electrode is in contact with the other upper limb of the human body; and determining electrocardiogram signals corresponding to twelve leads based on the potential signals of the surfaces of the two upper limbs and the lower limb of the human body and the potential signals of the surfaces of the six equivalent positions on the chest of the human body.

According to the second aspect, the electronic device further includes a display, configured to display the electrocardiogram signals corresponding to the twelve leads, so that a user can conveniently view the electrocardiogram signals of the twelve leads.

According to the second aspect or any implementation of the second aspect, when the computer program is executed by the one or more processors, the electronic device is enabled to perform the following step: processing the obtained potential signals of the surfaces of the two upper limbs and the lower limb of the human body to determine potential signals of six limb leads.

According to the second aspect or any implementation of the second aspect, when the computer program is executed by the one or more processors, the electronic device is enabled to perform the following steps: determining a lead I based on a potential difference between a potential signal of a surface of an upper left limb and a potential signal of a surface of an upper right limb; determining a lead II based on a potential difference between a potential signal of a surface of the lower limb and the potential signal of the surface of the upper right limb; determining a lead III based on a potential difference between the potential signal of the surface of the lower limb and the potential signal of the surface of the upper left limb; and determining a potential of the first center point, and determining a signal of a lead aVR, a signal of a lead aVL, and a signal of a lead aVF based on a potential difference between the potential of the first center point and the potential signal of the surface of the upper left limb, a potential difference between the potential of the first center point and the potential signal of the surface of the upper right limb, and a potential difference between the potential of the first center point and the potential signal of the surface of the lower limb.

According to the second aspect or any implementation of the second aspect, when the computer program is executed by the one or more processors, the electronic device is enabled to perform the following step: processing the obtained potential signals of the surfaces of the two upper limbs of the human body and the six equivalent positions on the chest of the human body to obtain signals of six chest leads.

According to the second aspect or any implementation of the second aspect, when the computer program is executed by the one or more processors, the electronic device is enabled to perform the following steps: determining a potential of the second center point, and determining a signal of a lead V1, a signal of a lead V2, a signal of a lead V3, a signal of a lead V4, a signal of a lead V5, and a signal of a lead V6 based on a potential difference between the potential of the second center point and a potential signal of a surface of each of the six equivalent positions on the chest of the human body.

According to the second aspect or any implementation of the second aspect, when the computer program is executed by the one or more processors, the electronic device is enabled to perform the following step: displaying a first interface, where the first interface includes a first information prompt box, and the first information prompt box is used to prompt the six equivalent positions on the chest.

According to the second aspect or any implementation of the second aspect, when the computer program is executed by the one or more processors, the electronic device is enabled to perform the following steps: obtaining a preview image that is of an upper body of the human body and that is captured by a camera; and determining target objects in the preview image in sequence, where the target objects include the six equivalent positions on the chest of the human body.

According to the second aspect or any implementation of the second aspect, when the computer program is executed by the one or more processors, the electronic device is enabled to perform the following step: outputting health status reminding information when the electrocardiogram signals corresponding to the twelve leads do not match preset electrocardiogram signals corresponding to the twelve leads.

The second aspect and any implementation of the second aspect respectively correspond to the first aspect and any implementation of the first aspect. For technical effects corresponding to the second aspect and any implementation of the second aspect, refer to the technical effects corresponding to the first aspect and any implementation of the first aspect. Details are not described herein again.

According to a third aspect, an embodiment of this application provides a multi-lead electrocardiogram detection system. The multi-lead electrocardiogram detection system includes: a smart wearable device and a mobile phone. The multi-lead electrocardiogram detection system further includes one or more processors, a memory, and one or more computer programs. The one or more computer programs are stored in the memory. When the computer program is executed by the one or more processors, an electronic device is enabled to perform the multi-lead electrocardiogram detection method according to the first aspect and any implementation of the first aspect.

The third aspect and any implementation of the third aspect respectively correspond to the first aspect and any implementation of the first aspect. For technical effects corresponding to the third aspect and any implementation of the third aspect, refer to the technical effects corresponding to the first aspect and any implementation of the first aspect. Details are not described herein again.

According to a fourth aspect, an embodiment of this application provides a computer-readable storage medium. The computer-readable storage medium includes a computer program. When the computer program is run on an electronic device, the electronic device is enabled to perform the multi-lead electrocardiogram detection method according to the first aspect and any implementation of the first aspect.

The fourth aspect and any implementation of the fourth aspect respectively correspond to the first aspect and any implementation of the first aspect. For technical effects corresponding to the fourth aspect and any implementation of the fourth aspect, refer to the technical effects corresponding to the first aspect and any implementation of the first aspect. Details are not described herein again.

According to a fifth aspect, an embodiment of this application provides a computer program product, including a computer program. When the computer program is run, a computer is enabled to perform the multi-lead electrocardiogram detection method according to the first aspect and any implementation of the first aspect.

The fifth aspect and any implementation of the fifth aspect respectively correspond to the first aspect and any implementation of the first aspect. For technical effects corresponding to the fifth aspect and any implementation of the fifth aspect, refer to the technical effects corresponding to the first aspect and any implementation of the first aspect. Details are not described herein again.

According to a sixth aspect, this application provides a chip. The chip includes a processing circuit and a transceiver pin. The transceiver pin and the processing circuit communicate with each other through an internal connection path. The processing circuit performs the multi-lead electrocardiogram detection method according to the first aspect or any implementation of the first aspect, to control a receiving pin to receive a signal, or control a sending pin to send a signal.

The sixth aspect and any implementation of the sixth aspect respectively correspond to the first aspect and any implementation of the first aspect. For technical effects corresponding to the sixth aspect and any implementation of the sixth aspect, refer to the technical effects corresponding to the first aspect and any implementation of the first aspect. Details are not described herein again.

DESCRIPTION OF EMBODIMENTS

The following clearly and completely describes the technical solutions in embodiments of this application with reference to the accompanying drawings in embodiments of this application. It is clear that the described embodiments are some but not all of embodiments of this application. All other embodiments obtained by a person of ordinary skill in the art based on embodiments of this application without creative efforts shall fall within the protection scope of this application.

The term "and/or" in this specification describes only an association relationship for describing associated objects and indicates that three relationships may exist. For example, A and/or B may indicate the following three cases: Only A exists, both A and B exist, and only B exists.

In this specification and claims in embodiments of this application, the terms "first", "second", and the like are intended to distinguish between different objects but do not indicate a particular order of the objects. For example, a first target object, a second target object, and the like are used to distinguish between different target objects, but are not used to describe a particular order of the target objects.

In embodiments of this application, the word such as "example" or "for example" is used to represent an example, an illustration, or a description. Any embodiment or design described as "example" or "for example" in embodiments of this application should not be construed as being more preferred or advantageous than another embodiment or design. To be precise, the word such as "example" or "for example" is intended to present a related concept in a specific manner.

In the descriptions of embodiments of this application, unless otherwise specified, "a plurality of" means two or more. For example, a plurality of processing units mean two or more processing units, and a plurality of systems mean two or more systems.

Figure 1:
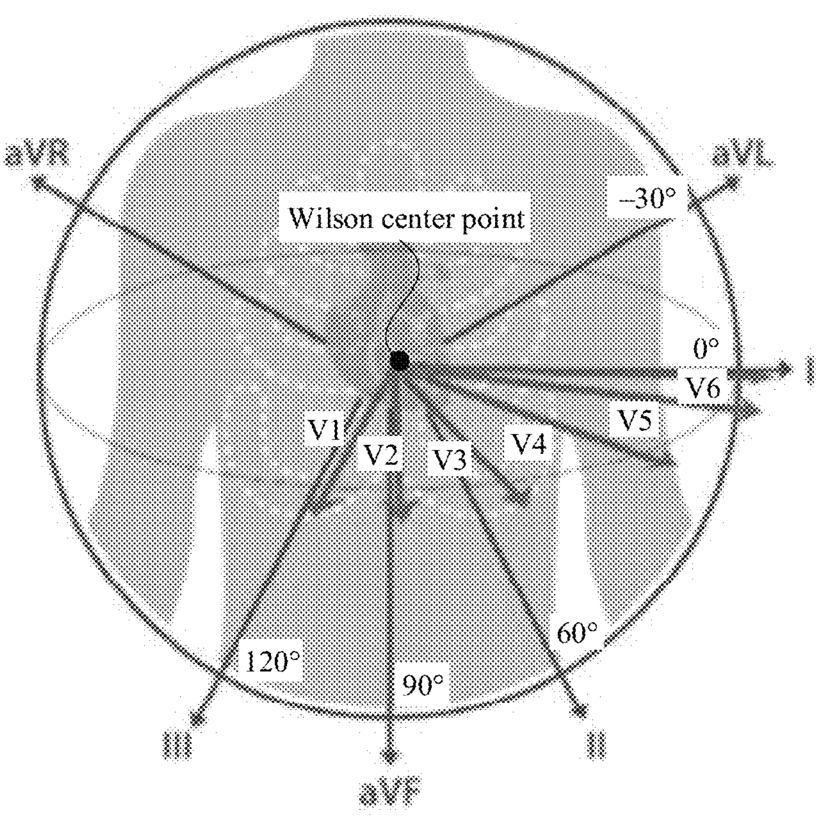
FIG. 1 is a diagram of a twelve-lead ECG according to an embodiment of this application.

Medically, a common lead system used for electrocardiogram measurement is a standard twelve-lead system. Refer to FIG. 1. A limb lead system reflects a condition of projection of a cardiac potential on a coronal plane (a longitudinal cross-section that divides a heart into a front part and a back part) and includes six limb leads: I, II, III, aVR, aVL, and aVF. A chest lead system reflects a condition of projection of the cardiac potential on a cross-section (a longitudinal cross-section that divides the heart into an upper part and a lower part) and includes six chest leads: V1, V2, V3, V4, V5, and V6.

Figure 2A:
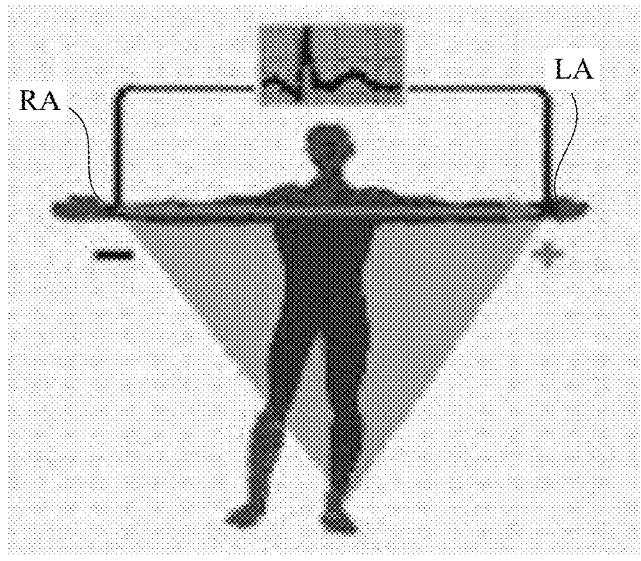
FIG. 2A to FIG. 2F are respectively diagrams of distribution of electrodes corresponding to six limb leads.
Figure 2B:
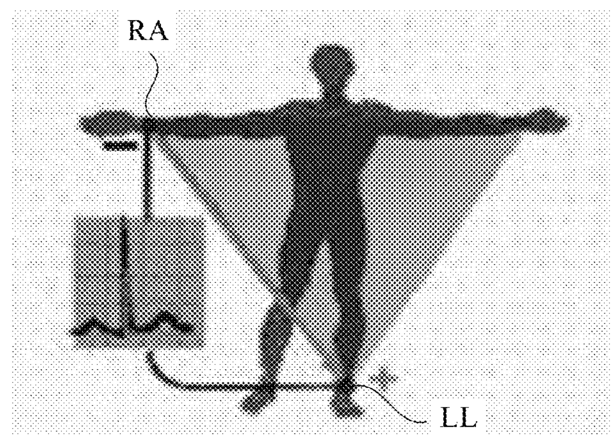
Figure 2C:
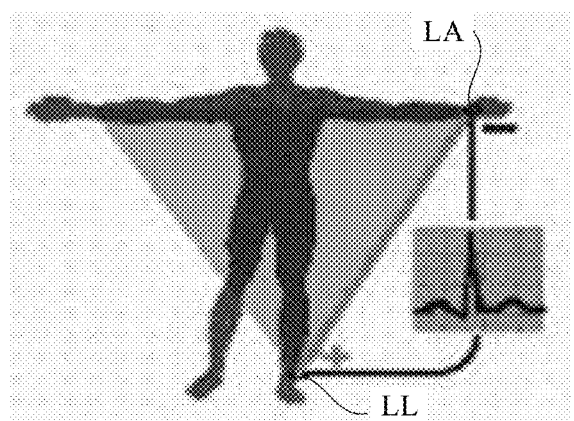
Figure 2D:
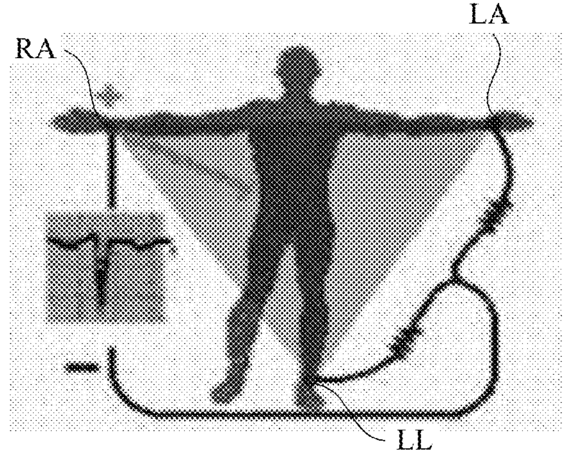
Figure 2E:
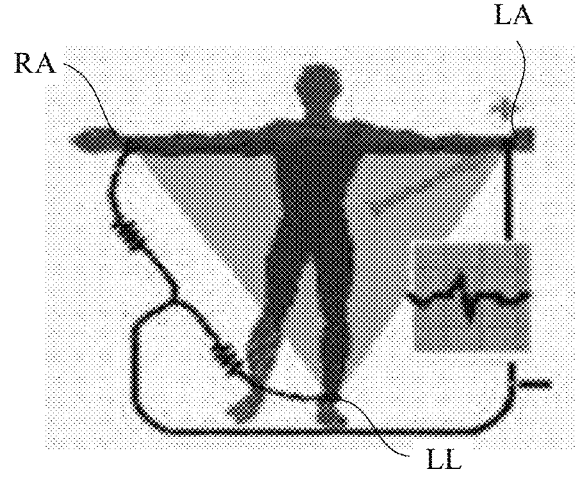
Figure 2F:
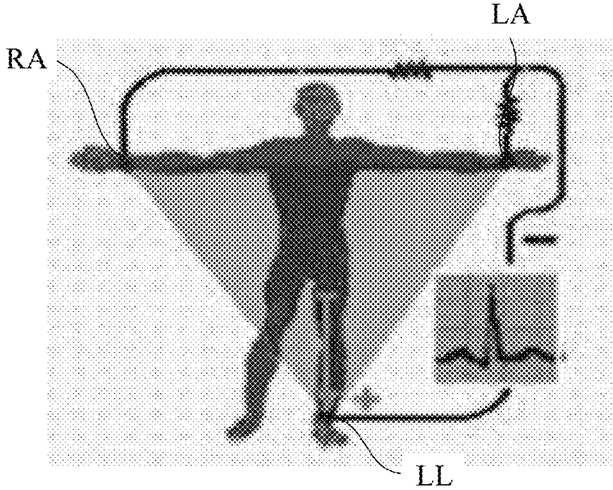

With reference to FIG. 2A to FIG. 2F, detection of the six limb leads is, respectively, forming an electrocardiogram signal corresponding to a limb lead I (as shown in FIG. 2A) based on a potential difference between an upper left limb electrode LA and an upper right limb electrode RA, forming an electrocardiogram signal corresponding to a limb lead II (as shown in FIG. 2B) based on a potential difference between the upper right limb electrode RA and a lower limb electrode LL, and forming an electrocardiogram signal corresponding to a limb lead III (as shown in FIG. 2C) based on a potential difference between the upper left limb electrode LA and the lower limb electrode LL. A potential of a center, that is, a Wilson center point, of the upper left limb electrode LA, the upper right limb electrode RA, and the lower limb electrode LL may be positioned by using the upper left limb electrode LA, the upper right limb electrode RA, and the lower limb electrode LL at the same time, and a potential difference between Wilson and each of the three electrodes is detected to form electrocardiogram signals corresponding to three limb leads: aVR (as shown in FIG. 2D), aVL (as shown in FIG. 2E), and aVF (as shown in FIG. 2F).

In this embodiment of this application, "upper limbs" mean a part under shoulders and include hands; and "lower limbs" mean a part under the navel and include feet, lower abdomen, legs, knees, and the like. In addition, because accurate potential signals may also be obtained by using a right lower limb in place of a left lower limb for electrocardiogram measurement, the "lower limb" in this specification means either the left lower limb or the right lower limb.

Figure 3:
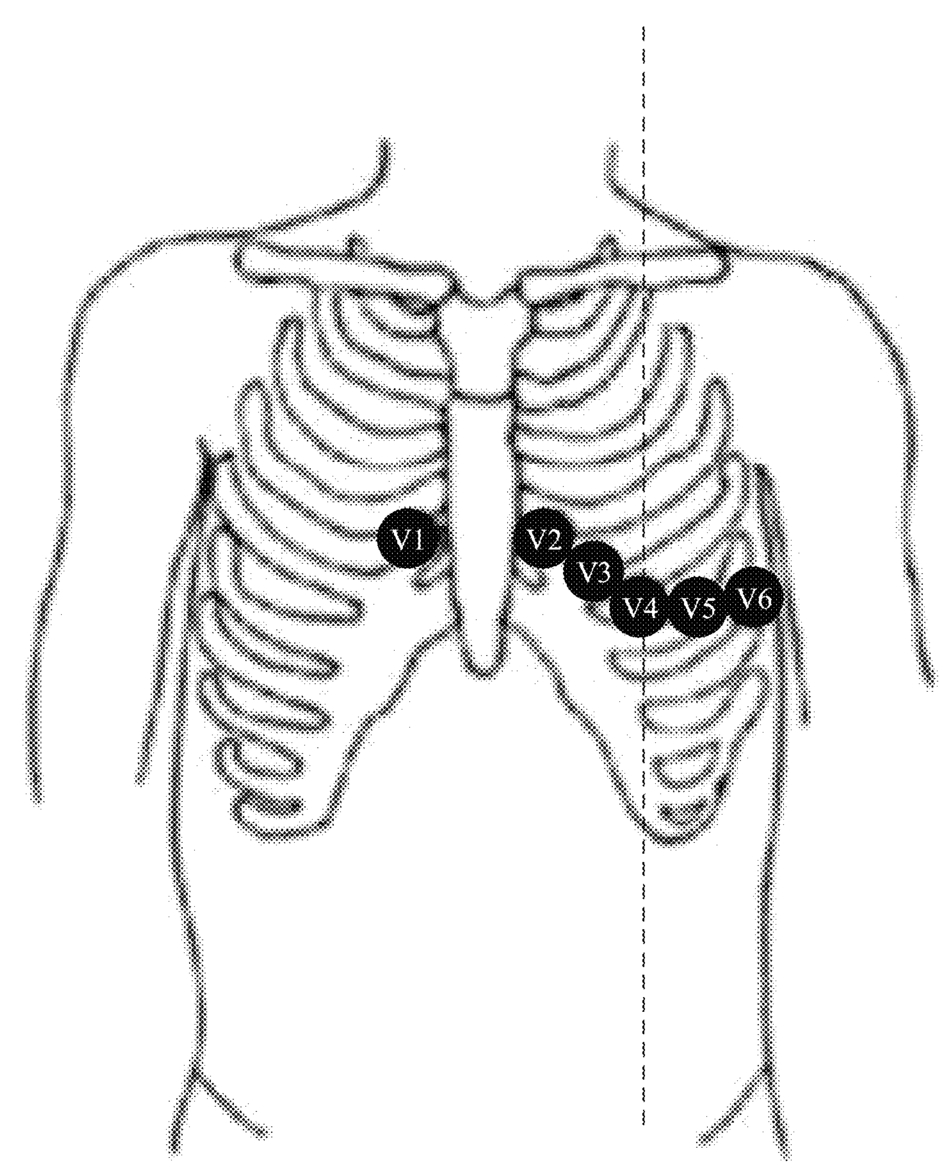
FIG. 3 is a diagram of distribution of electrodes corresponding to six chest leads.

Refer to FIG. 1 and FIG. 3. Detection of the six chest leads depends on the Wilson center point determined by using the upper left limb electrode LA, the upper right limb electrode RA, and the lower limb electrode LL, and also depends on a total of six electrodes: V1, V2, V3, V4, V5, and V6 placed at six positions on the chest. Signals of six leads V1, V2, V3, V4, V5, and V6 are formed based on potential difference vectors point from the Wilson center point to the six chest electrodes.

V1 is located at the fourth intercostal space to the right of the sternum (that is, a first preset position), V2 is located at the fourth intercostal space to the left of the sternum (that is, a second preset position), V3 is located at a midpoint of a connection line between V2 and V4 (that is, a third preset position), V4 is located at an intersection of the left midclavicular line and the fifth intercostal space (that is, a fourth preset position), V5 is located at a position that is on the left anterior axillary line and that is at a same horizontal level as V4 (that is, a fifth preset position), and V6 is located at a position that is on the left midclavicular line and that is at the same horizontal level as V4 (that is, a sixth preset position).

Figure 4:
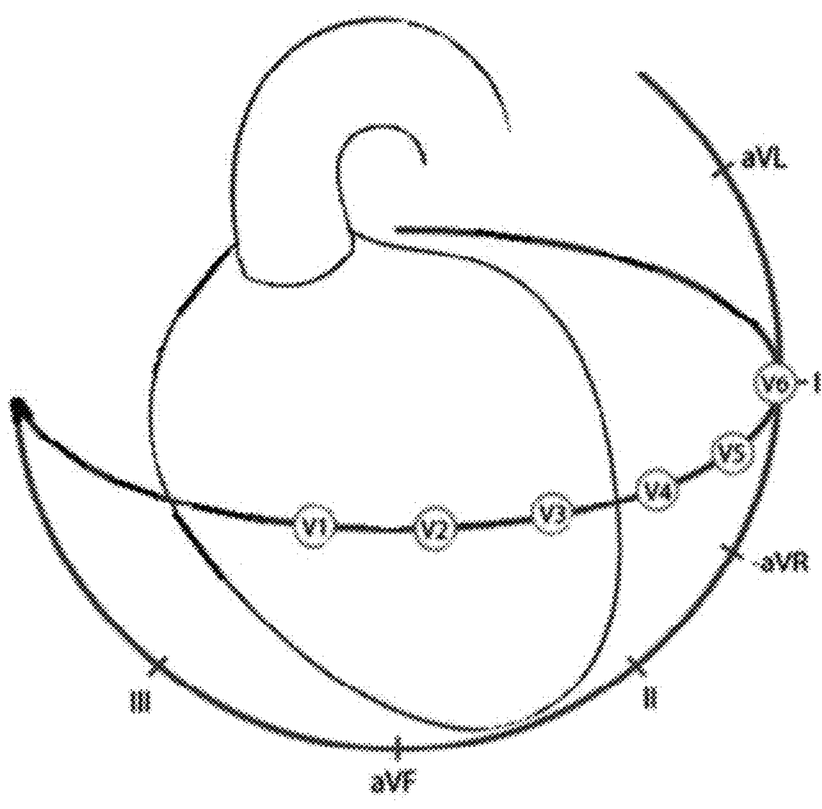
FIG. 4 is another diagram of a twelve-lead ECG according to an embodiment of this application.

With reference to FIG. 4, one lead represents a detection vector in one direction. A single detection vector can only detect an anomaly in one direction. An electrocardiogram used for medical diagnosis relates to detection of the six leads (I, II, III, aVL, aVF, and aVR) on the coronal plane and the six leads (V1, V2, V3, V4, V5, and V6) on the cross-section, that is, twelve-lead detection. This can cover common onset positions of acute myocardial infarction.

Medical electrocardiograph equipment can implement twelve-lead detection. However, the medical electrocardiograph equipment is large, needs to be operated by professional medical personnel, and cannot detect diseases such as acute myocardial infarction in a timely manner. An ECG detection function of existing portable devices mainly relates to single-lead ECG detection, and single-lead ECG detection can only detect time series anomalies (such as atrial fibrillation and a premature beat) of electrocardiogram signals, but cannot effectively detect scenarios, such as acute myocardial infarction, that need to be detected by using a multi-lead ECG.

Figure 5:
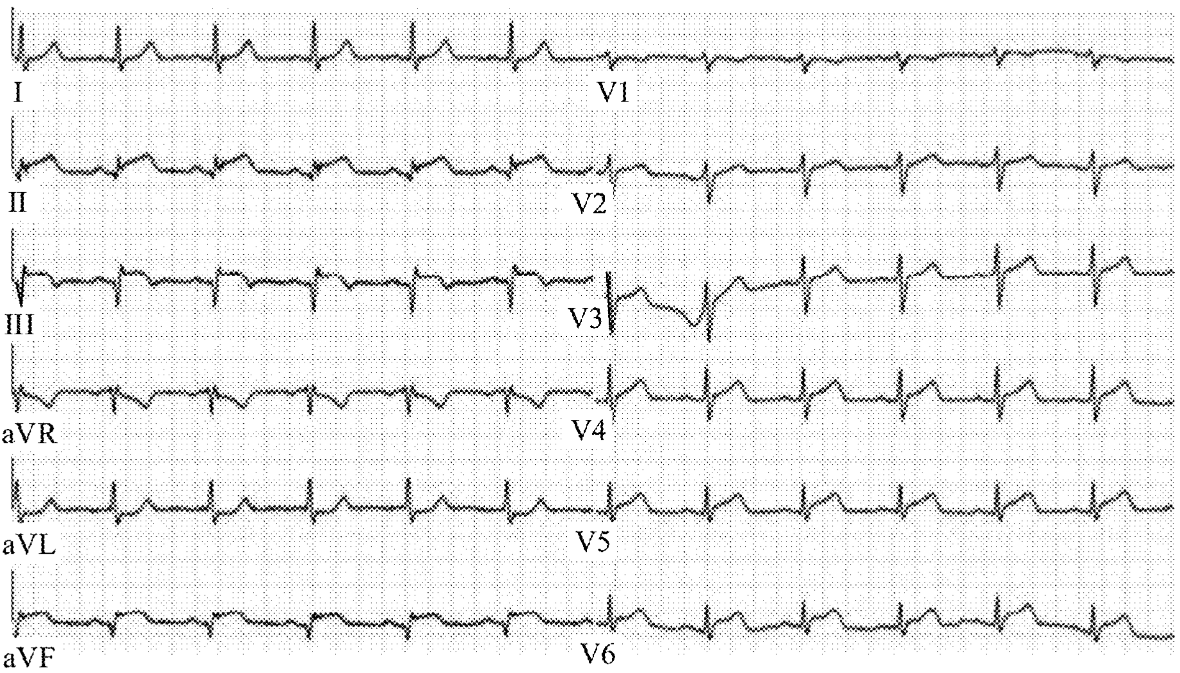
FIG. 5 is an electrocardiogram corresponding to six limb leads.

For example, the ECG detection function integrated on some bands in the conventional technology can obtain a potential signal corresponding to a lead I of both hands. Refer to FIG. 5. Detection of the lead I is normal, but an electrocardiogram of another lead shows a typical ST segment change of acute myocardial infarction. In this scenario, if only the lead I is used for detection, detection of acute myocardial infarction may be missed. The scenarios, such as acute myocardial infarction, that need to be detected by using the multi-lead ECG cannot be effectively detected.

Based on this, an embodiment of this application provides a multi-lead electrocardiogram detection method and an electronic device. The electronic device is provided with three electrodes used for collecting electrical signals on a surface of a human body. Two of the three electrodes are in contact with two upper limbs of a user, and the other electrode touches a lower limb position and six equivalent positions on a chest in sequence (for example, touch duration is 10 s). The six equivalent positions on the chest are six positions obtained after six positions (that is, the first preset position, the second preset position, the third preset position, the fourth preset position, the fifth preset position, and the sixth preset position) on the chest move directly upward (in directions of the two upper limbs) by a preset distance. The preset distance is a distance between the Wilson center point determined when two of the three electrodes are in contact with the two upper limbs of the user, and the other electrode is in contact with a lower limb and a center point determined when the two electrodes are in contact with the two upper limbs of the user. In addition, an electrical signal at each position is collected. The electronic device may obtain potential signals corresponding to six limb leads based on the collected electrical signals of the two upper limbs and one lower limb of the human body, and the electronic device may obtain potential signals corresponding to six chest leads based on the collected electrical signals of the two upper limbs of the human body and the six equivalent positions on the chest, to implement twelve-lead ECG measurement. Because twelve-lead ECG detection can cover common onset positions of acute myocardial infarction, in this embodiment of this application, not only time series anomalies (such as atrial fibrillation and a premature beat) of electrocardiogram signals can be detected, but the scenarios, such as acute myocardial infarction, that need to be detected by using the multi-lead ECG can also be effectively detected in a timely manner. In addition, in this embodiment of this application, only three electrodes are used to implement twelve-lead ECG measurement, a structure is simple, and a short time is consumed (for example, twelve-lead ECG measurement may be completed in 70 s).

In embodiments of this application, the electronic device may be, for example, a smart wearable device (such as a smartwatch, a smart band, and a smart arm band), a mobile phone, a tablet computer, or the like. A specific form of the foregoing electronic device is not specifically limited in embodiments of this application.

The following uses a smartwatch as an example to describe a structure of an electronic device provided in this embodiment of this application and a principle for implementing twelve-lead ECG measurement.

Figure 6:
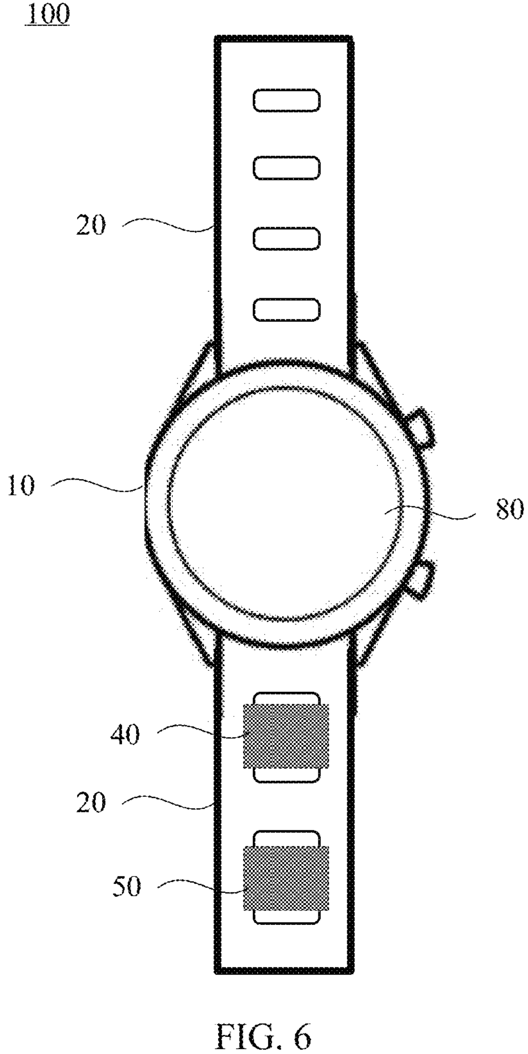
FIG. 6 is a diagram of a front-side structure of an electronic device.
Figure 7:
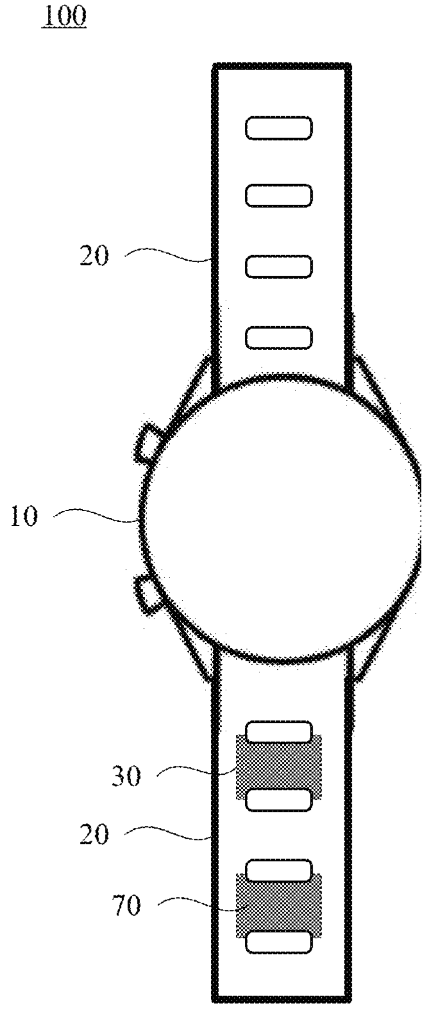
FIG. 7 is a diagram of a back-side structure of an electronic device.

FIG. 6 is a diagram of a front-side structure of the electronic device. FIG. 7 is a diagram of a back-side structure of the electronic device. As shown in FIG. 6 and FIG. 7, the smartwatch 100 may include a watch body 10 and a wristband 20 connected to the watch body 10. The wristband 20 is configured to put the watch body 10 on a wrist of a user.

The smartwatch 100 further includes three detection electrodes disposed on a surface of the smartwatch 100, so that the three detection electrodes are in contact with a surface of a human body. The three detection electrodes are respectively a first detection electrode 30, a second detection electrode 40, and a third detection electrode 50. The first detection electrode 30 is configured to be in contact with one upper limb (for example, an upper left limb) of the human body, the second detection electrode 40 is configured to be in contact with the other upper limb (for example, an upper right limb) of the human body, and the third detection electrode 50 is configured to be in contact with a lower limb of the human body and six equivalent positions on a chest in sequence. The six equivalent positions on the chest are respectively a first equivalent position, a second equivalent position, a third equivalent position, a fourth equivalent position, a fifth equivalent position, and a sixth equivalent position. The following describes in detail specific positions of the six equivalent positions. Details are not described herein again.

Figure 8:
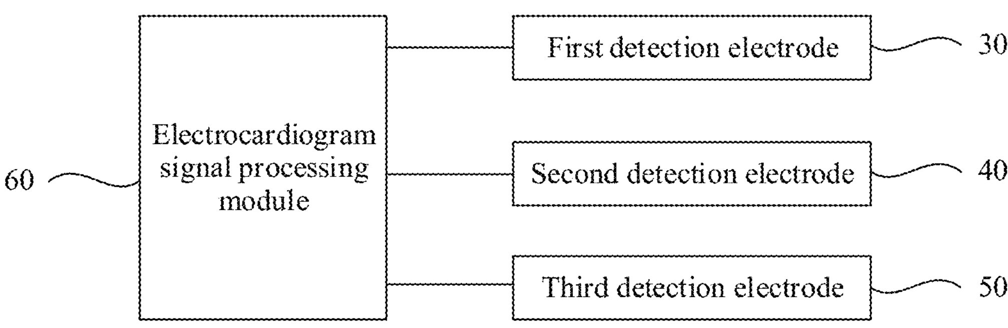
FIG. 8 is a diagram of a circuit structure of an electronic device.

FIG. 8 is a diagram of a circuit structure of the electronic device. As shown in FIG. 8, the smartwatch 100 further includes an electrocardiogram signal processing module 60 disposed, for example, in the watch body 10. The electrocardiogram signal processing module 60 is electrically connected to the first detection electrode 30, the second detection electrode 40, and the third detection electrode 50 respectively. The electrocardiogram signal processing module 60 may be a micro-control unit or another unit that has a signal processing function.

When the first detection electrode 30 is in contact with one upper limb (for example, the upper left limb) of the human body, the second detection electrode 40 is in contact with the other upper limb (for example, the upper right limb) of the human body, and the third detection electrode 50 is in contact with the lower limb of the human body, the first detection electrode 30, the second detection electrode 40, and the third detection electrode 50 collect potential signals of surfaces of respective corresponding limbs. The electrocardiogram signal processing module 60 collects the potential signals on the detection electrodes and processes the received potential signals to generate electrocardiogram signals corresponding to six limb leads. In some embodiments, the electrocardiogram signal processing module 60 collects the potential signals on the detection electrodes and processes the received potential signals to obtain a potential difference between the electrodes, and the potential difference between the electrodes is amplified through an amplifier circuit, to obtain the electrocardiograph signals corresponding to the limb leads.

Specifically, an electrocardiogram signal corresponding to a lead I may be determined based on a potential difference between a potential signal of a surface of the upper left limb and a potential signal of a surface of the upper right limb; an electrocardiogram signal corresponding to a lead II may be determined based on a potential difference between a potential signal of a surface of the lower limb and the potential signal of the surface of the upper right limb; and an electrocardiogram signal corresponding to a lead III may be determined based on a potential difference between the potential signal of the surface of the lower limb and the potential signal of the surface of the upper left limb.

A potential of a Wilson center point (also referred to as a first center point T1) of the three electrodes may be positioned based on the potential signal of the surface of the upper left limb, the potential signal of the surface of the upper right limb, and the potential signal of the surface of the lower limb, and an electrocardiogram signal corresponding to a lead aVR, an electrocardiogram signal corresponding to a lead aVL, and an electrocardiogram signal corresponding to a lead aVF are determined based on a potential difference between the potential of the first center point T1 and the potential signal of the surface of the upper left limb, a potential difference between the potential of the first center point T1 and the potential signal of the surface of the upper right limb, and a potential difference between the potential of the first center point T1 and the potential signal of the surface of the lower limb, so that the electrocardiogram signals corresponding to the six limb leads can be obtained.

Figure 9:
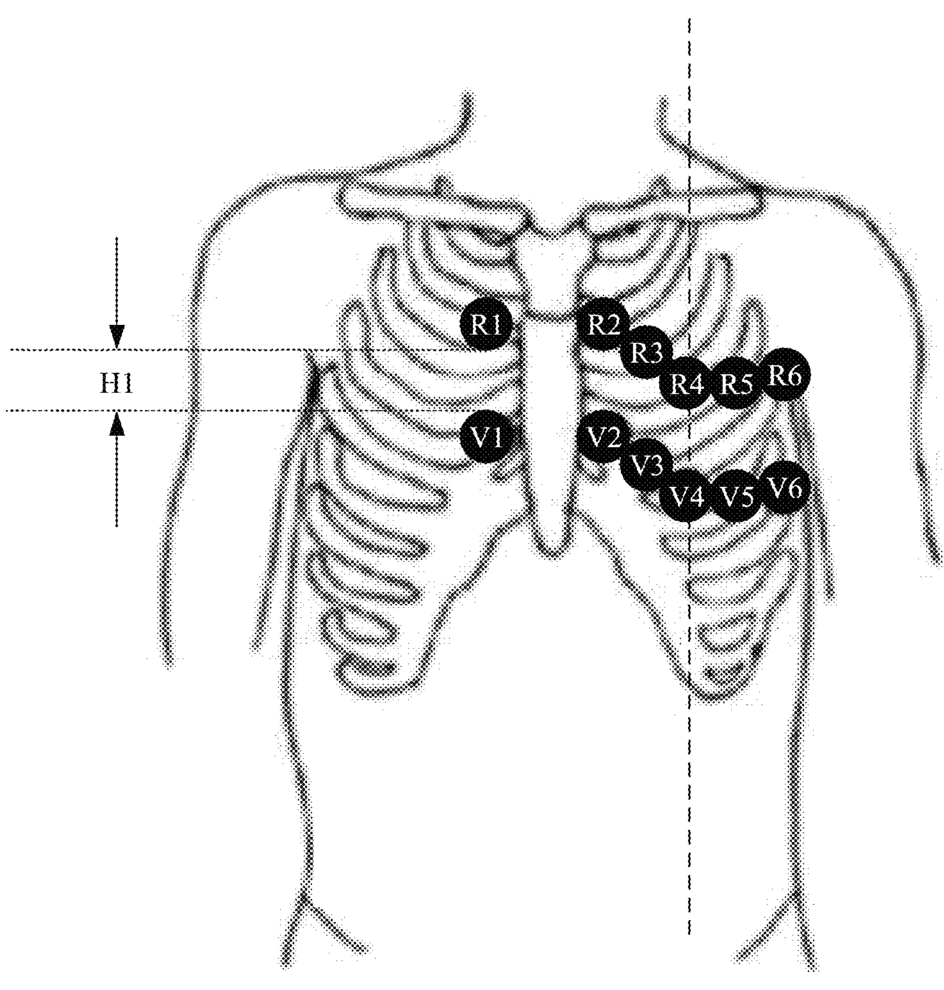
FIG. 9 is a comparison diagram of six preset positions and six equivalent positions on the chest.
Figure 10:
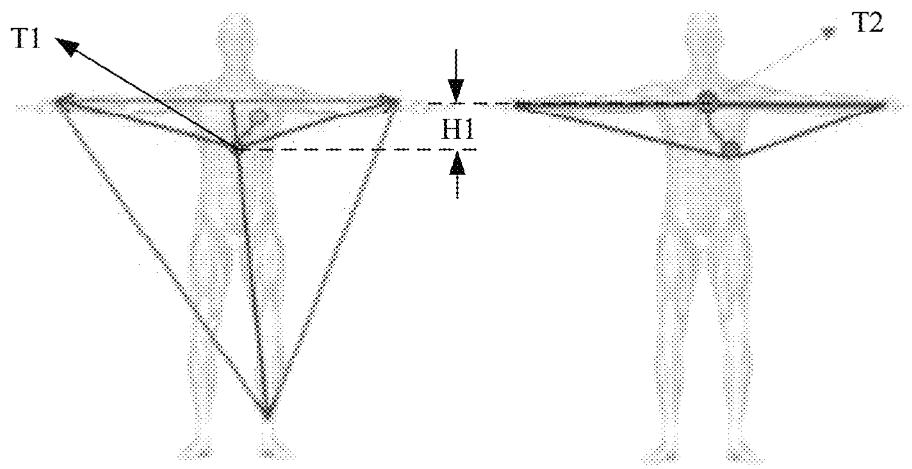
FIG. 10 is a principle diagram of determining a preset distance.

FIG. 9 is a comparison diagram of six preset positions and the six equivalent positions on the chest. As shown in FIG. 9, when the first detection electrode 30 is in contact with one upper limb (for example, the upper left limb) of the human body, the second detection electrode 40 is in contact with the other upper limb (for example, the upper right limb) of the human body, and the third detection electrode 50 is in contact with the first equivalent position R1 (contact duration is, for example, 10 s), the first detection electrode 30, the second detection electrode 40, and the third detection electrode 50 collect the potential signals of the surfaces of the respective corresponding limbs. The electrocardiogram signal processing module 60 collects the potential signals on the detection electrodes and processes the received potential signals to generate an electrocardiogram signal corresponding to a chest lead V1. In some embodiments, the electrocardiogram signal processing module 60 collects the potential signals on the detection electrodes and processes the received potential signals to obtain the potential difference between the electrodes, and the potential difference between the electrodes is amplified through the amplifier circuit, to obtain the electrocardiograph signal corresponding to the chest lead V1. The first equivalent position R1 is a position obtained after a first preset position V1 on the chest (the fourth intercostal space to the right of the sternum) moves directly upward (in directions of the two upper limbs) by a preset distance H1. FIG. 10 is a principle diagram of determining the preset distance. As shown in FIG. 10, the preset distance H1 is a distance between the first center point T1 determined when the first detection electrode 30 is in contact with one upper limb of the human body, the second detection electrode 40 is in contact with the other upper limb of the human body, and the third detection electrode 50 is in contact with the lower limb of the human body and a second center point T2 determined when the first detection electrode is in contact with one upper limb of the human body, and the second detection electrode is in contact with the other upper limb of the human body.

Figure 11:
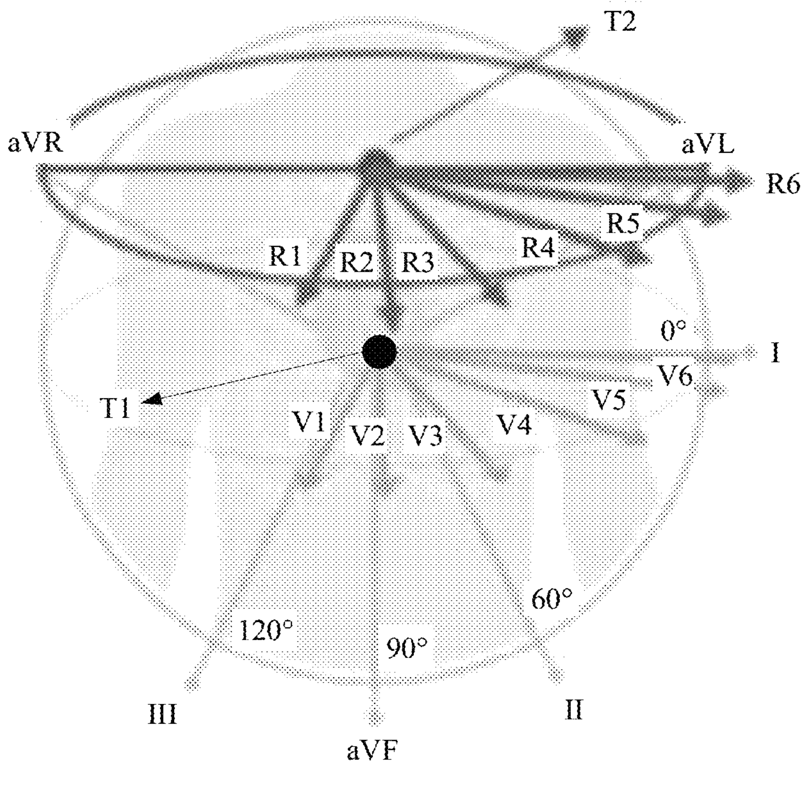
FIG. 11 is a diagram of equivalent chest lead detection.

This is because: FIG. 11 is a diagram of equivalent chest lead detection, and as shown in FIG. 11, a vector direction in which the second center point T2 determined when the first detection electrode is in contact with one upper limb of the human body, and the second detection electrode is in contact with the other upper limb of the human body points to the first equivalent position R1 is in a one-to-one correspondence with a vector direction in which the first center point T1 determined when the first detection electrode is in contact with one upper limb of the human body, the second detection electrode is in contact with the other upper limb of the human body, and the third detection electrode is in contact with the lower limb of the human body points to the first preset position V1 on the chest. Therefore, in this scenario, a lead at the first equivalent position on the chest may be considered as an equivalent lead of a lead at the first preset position on the chest, so that detection of an equivalent lead of a chest lead V1 is implemented.

Similarly, refer to FIG. 9, FIG. 10, and FIG. 11. When the first detection electrode 30 is in contact with one upper limb (for example, the upper left limb) of the human body, the second detection electrode 40 is in contact with the other upper limb (for example, the upper right limb) of the human body, and the third detection electrode 50 is in contact with the second equivalent position R2, the third equivalent position R3, the fourth equivalent position R4, the fifth equivalent position R5, and the sixth equivalent position R6 in sequence (contact duration is, for example, 10 s), the first detection electrode 30, the second detection electrode 40, and the third detection electrode 50 collect the potential signals of the surfaces of the respective corresponding limbs. The electrocardiogram signal processing module 60 collects the potential signals on the detection electrodes and processes the received potential signals to generate an electrocardiogram signal corresponding to a chest lead V2, an electrocardiogram signal corresponding to a chest lead V3, an electrocardiogram signal corresponding to a chest lead V4, an electrocardiogram signal corresponding to a chest lead V5, and an electrocardiogram signal corresponding to a chest lead V6. In some embodiments, the electrocardiogram signal processing module 60 collects the potential signals on the detection electrodes and processes the received potential signals to obtain potential differences between the electrodes, and the potential differences between the electrodes is amplified through the amplifier circuit, to obtain the electrocardiogram signal corresponding to the chest lead V2, the electrocardiogram signal corresponding to the chest lead V3, the electrocardiogram signal corresponding to the chest lead V4, the electrocardiogram signal corresponding to the chest lead V5, and the electrocardiogram signal corresponding to the chest lead V6.

The second equivalent position R2 is a position obtained after a second preset position V2 on the chest (the fourth intercostal space to the left of the sternum) moves in directions of the two upper limbs by the preset distance H1. The third equivalent position R3 is a position obtained after a third preset position V3 on the chest (a midpoint of a connection line between the second preset position and a fourth preset position) moves in the directions of the two upper limbs by the preset distance H1. The fourth equivalent position R4 is a position obtained after the fourth preset position V4 on the chest (an intersection of the left midclavicular line and the fifth intercostal space) moves in the directions of the two upper limbs by the preset distance H1. The fifth equivalent position R5 is a position obtained after a fifth preset position V5 on the chest (a position that is on the left anterior axillary line and that is at a same horizontal level as the fourth preset position) moves in the directions of the two upper limbs by the preset distance H1. The sixth equivalent position R6 is a position obtained after a sixth preset position V6 on the chest (a position that is on the left midclavicular line and that is at the same horizontal level as the fourth preset position) moves in the directions of the two upper limbs by the preset distance H1. The preset distance H1 is the distance between the first center point T1 determined when the first detection electrode 30 is in contact with one upper limb of the human body, the second detection electrode 40 is in contact with the other upper limb of the human body, and the third detection electrode 50 is in contact with the lower limb of the human body and the second center point T2 determined when the first detection electrode 30 is in contact with one upper limb of the human body, and the second detection electrode 40 is in contact with the other upper limb of the human body.

This is because a vector direction in which the second center point T2 determined when the first detection electrode 30 is in contact with one upper limb of the human body, and the second detection electrode 40 is in contact with the other upper limb of the human body points to the second equivalent position R2, a vector direction in which the second center point T2 points to the third equivalent position R3, a vector direction in which the second center point T2 points to the fourth equivalent position R4, a vector direction in which the second center point T2 points to the fifth equivalent position R5, and a vector direction in which the second center point T2 points to the sixth equivalent position R6 are in a one-to-one correspondence with a vector direction in which the first center point T1 determined when the first detection electrode 30 is in contact with one upper limb of the human body, the second detection electrode 40 is in contact with the other upper limb of the human body, and the third detection electrode 50 is in contact with the lower limb of the human body points to the second preset position V2 on the chest, a vector direction in which the first center point T1 points to the third preset position V3 on the chest, a vector direction in which the first center point T1 points to the fourth preset position V4 on the chest, a vector direction in which the first center point T1 points to the fifth preset position V5 on the chest, and a vector direction in which the first center point points to the sixth preset position V6 on the chest. Therefore, in this scenario, a lead at the second equivalent position, a lead at the third equivalent position, a lead at the fourth equivalent position, a lead at the fifth equivalent position, and a lead at the sixth equivalent position on the chest may be considered as equivalent leads of a lead at the first preset position, a lead at the second preset position, a lead at the third preset position, a lead at the fourth preset position, a lead at the fifth preset position, and a lead at the sixth preset position on the chest, so that detection of equivalent leads of chest leads V1, V2, V3, V4, V5, and V6 is implemented. Therefore, electrocardiogram signals corresponding to six chest leads are obtained.

In conclusion, twelve-lead ECG measurement may be implemented by using the three electrodes. Scenarios, such as acute myocardial infarction, that need to be detected by using the multi-lead ECG may be effectively detected in a timely manner, and a structure is simple.

It may be understood that, in actual use, two of the three detection electrodes may be respectively in contact with the two upper limbs of the human body, and the other electrode is in contact with one lower limb and the six equivalent positions on the chest in sequence to obtain the electrocardiogram signals corresponding to the six limb leads and the six chest leads; or two of the three detection electrodes may be respectively in contact with the two upper limbs of the human body, and the other detection electrode is in contact with one lower limb to obtain the electrocardiogram signals corresponding to the six limb leads; or two of the three detection electrodes may be respectively in contact with limbs of the human body, and the other detection electrode is not used, so that an electrocardiogram signal corresponding to one limb lead (for example, the lead I) may be obtained.

In some embodiments, still refer to FIG. 7. The smartwatch 100 further includes a fourth detection electrode 70 disposed on the surface of the smartwatch 100, so that the fourth detection electrode 70 is in contact with the surface of the human body. The fourth detection electrode 70 serves as a drive electrode and is configured to eliminate common-mode interference.

Positions of the four electrodes (to be specific, three detection electrodes and one drive electrode) are not limited in this embodiment of this application provided that, in a use process of the user, the four electrodes can be in contact with the foregoing positions conveniently.

In a possible implementation, still refer to FIG. 6 and FIG. 7. Two electrodes are disposed on an inner side of the wristband 20 and are respectively the first detection electrode 30 and the fourth detection electrode 70, and two electrodes are disposed on an outer side of the wristband 20 and are respectively the second detection electrode 40 and the third detection electrode 50.

Figure 12:
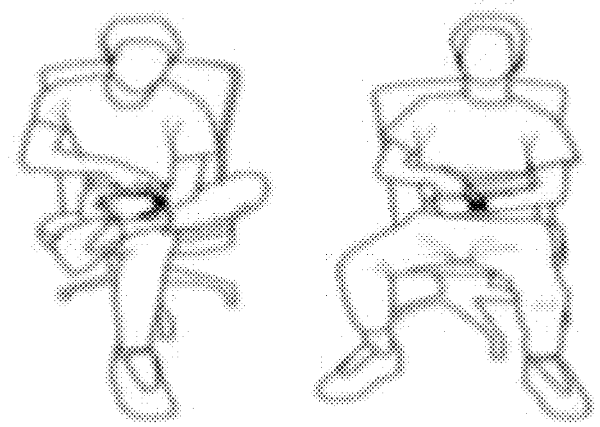
FIG. 12 is a diagram 1 of a use scenario of an electronic device.

In this case, FIG. 12 is a diagram of a use scenario of the electronic device. As shown in FIG. 12, when using the smartwatch 100 for twelve-lead ECG detection, the user may wear the smartwatch 100 on a left hand. The first detection electrode 30 can be in contact with a left wrist of the user naturally to detect a potential signal of the left hand. The fourth detection electrode 70 serves as the drive electrode. In addition, because the second detection electrode 40 and the third detection electrode 50 are located on the outer side of the wristband, during detection, a right hand touches the second detection electrode 40 to detect a potential signal of the right hand. On a premise that the first detection electrode 30 is in contact with the left wrist, and the second detection electrode 40 is in contact with the right hand, the third detection electrode 50 is in contact with the lower limb, the first equivalent position R1, the second equivalent position R2, the third equivalent position R3, the fourth equivalent position R4, the fifth equivalent position R5, and the sixth equivalent position R6 in sequence to detect potential signals of the lower limb, the first equivalent position R1, the second equivalent position R2, the third equivalent position R3, the fourth equivalent position R4, the fifth equivalent position R5, and the sixth equivalent position R6, so as to determine a twelve-lead ECG based on the foregoing potential signals.

To help the user quickly determine the first equivalent position R1, the second equivalent position R2, the third equivalent position R3, the fourth equivalent position R4, the fifth equivalent position R5, and the sixth equivalent position R6, optionally, still refer to FIG. 6 and FIG. 7. The smartwatch 100 further includes a display 80. The display 80 may be configured to display a first interface. The first interface includes a first information prompt box. The first information prompt box is used to prompt the six equivalent positions on the chest. The user may place the third detection electrode 50 based on a prompt, to complete detection, improve user experience, and improve accuracy of detection.

In addition, electrocardiogram signals of twelve leads may further be displayed through the display 80, to facilitate viewing of the user.

Certainly, a manner for helping the user quickly determine the first equivalent position R1, the second equivalent position R2, the third equivalent position R3, the fourth equivalent position R4, the fifth equivalent position R5, and the sixth equivalent position R6 is not limited thereto, and may be set by a person skilled in the art according to an actual requirement. This is not specifically limited in this embodiment of this application.

In another optional embodiment, the smartwatch 100 further includes a camera. The camera may capture a preview image of an upper body of the human body, where the preview image of the upper body may be a preview image above an abdomen. Target objects in the preview image are determined in sequence based on the preview image that is of the upper body of the human body and that is captured by the camera, where the target objects include the six equivalent positions on the chest of the human body.

Figure 13:
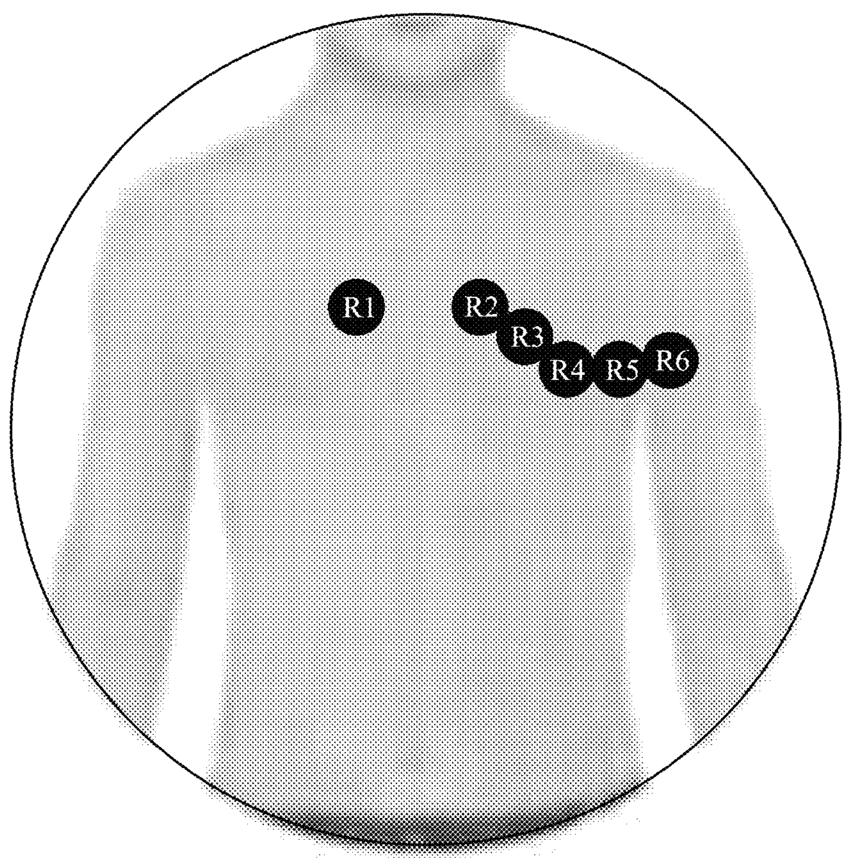
FIG. 13 is a diagram of displaying a preview picture.

Specifically, during actual application, FIG. 13 is a diagram of displaying the preview picture. As shown in FIG. 13, when the user enters a camera photographing mode of the smartwatch 100, the camera photographing mode becomes a photographing preview mode, and the preview picture is displayed. The six equivalent positions on the chest (the first equivalent position R1, the second equivalent position R2, the third equivalent position R3, the fourth equivalent position R4, the fifth equivalent position R5, and the sixth equivalent position R6) in the preview picture are locked by identifying feature information such as shoulders and the chest in a photographing preview picture, and are displayed to the user. The user may place the third detection electrode 50 based on the prompt, to complete detection, improve user experience, and improve accuracy of detection.

In addition, an embodiment of this application further provides a multi-lead electrocardiogram detection method. For example, the multi-lead electrocardiogram detection method may be applied to an electronic device (such as a smartwatch) in this embodiment, and has same beneficial effect. For detailed content that is not described in detail in this embodiment, refer to the foregoing embodiments of the electronic device. The following describes the multi-lead electrocardiogram detection method with reference to the accompanying drawings of the foregoing embodiments.

Figure 14:
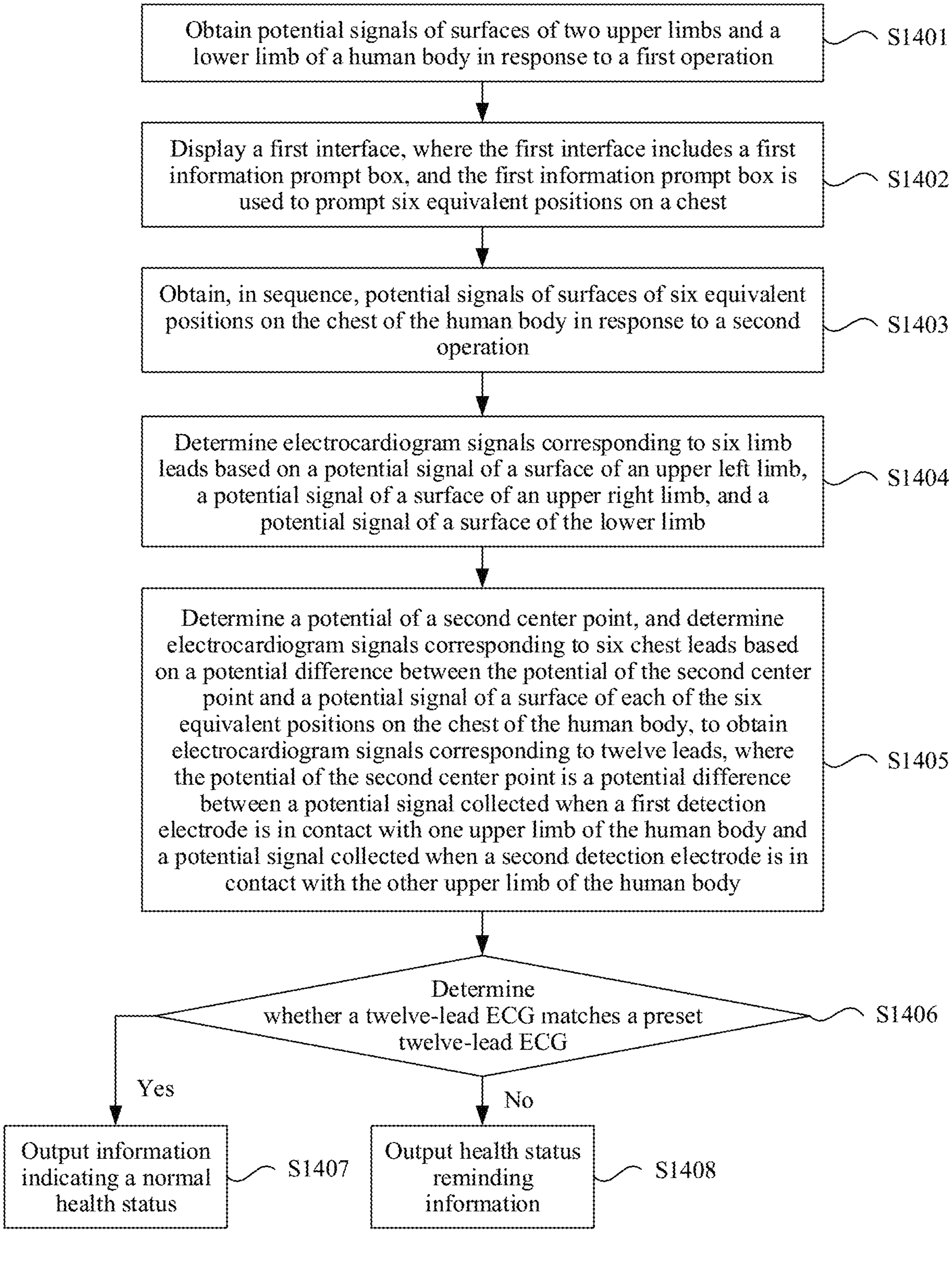
FIG. 14 is a flowchart of a multi-lead electrocardiogram detection method.

FIG. 14 is a flowchart of the multi-lead electrocardiogram detection method. As shown in FIG. 14, the multi-lead electrocardiogram detection method specifically includes the following steps.

S1401: Obtain potential signals of surfaces of two upper limbs and a lower limb of a human body in response to a first operation, where the first operation is an operation that a first detection electrode is in contact with one upper limb of the human body, a second detection electrode is in contact with the other upper limb of the human body, and a third detection electrode is in contact with the lower limb of the human body.

When the first detection electrode 30 is in contact with one upper limb (for example, an upper left limb) of the human body, the second detection electrode 40 is in contact with the other upper limb (for example, an upper right limb) of the human body, and the third detection electrode 50 is in contact with the lower limb of the human body, the first detection electrode 30, the second detection electrode 40, and the third detection electrode 50 collect potential signals of surfaces of respective corresponding limbs.

S1402: Display a first interface, where the first interface includes a first information prompt box, and the first information prompt box is used to prompt six equivalent positions on a chest. The following describes in detail specific positions of the six equivalent positions. Details are not described herein again.

While the first detection electrode 30 is in contact with one upper limb (for example, the upper left limb) of the human body, and the second detection electrode 40 is in contact with the other upper limb (for example, the upper right limb), a user may place the third detection electrode 50 at the six equivalent positions on the chest based on a prompt, to complete detection of six chest leads, improve user experience, and improve accuracy of detection.

Certainly, a manner for helping the user quickly determine a first equivalent position R1, a second equivalent position R2, a third equivalent position R3, a fourth equivalent position R4, a fifth equivalent position R5, and a sixth equivalent position R6 is not limited thereto, and may be set by a person skilled in the art according to an actual requirement. This is not specifically limited in this embodiment of this application.

Alternatively, step S1402 may be: obtaining a preview image captured by a camera; and determining target objects in the preview image in sequence, where the target objects include the six equivalent positions on the chest of the human body. Specifically, when the user enters a camera photographing mode of the smartwatch 100, the camera photographing mode becomes a photographing preview mode, and the preview picture is displayed. The six equivalent positions on the chest (the first equivalent position R1, the second equivalent position R2, the third equivalent position R3, the fourth equivalent position R4, the fifth equivalent position R5, and the sixth equivalent position R6) in the preview picture are locked by identifying feature information such as shoulders and the chest in a photographing preview picture, and are displayed to the user. The user may place the third detection electrode 50 based on the prompt, to complete detection, improve user experience, and improve accuracy of detection.

S1403: Obtain, in sequence, potential signals of surfaces of the six equivalent positions on the chest of the human body in response to a second operation, where the second operation is an operation that the third detection electrode is in contact with the six equivalent positions on the chest of the human body in sequence, the six equivalent positions on the chest are six positions obtained after six preset positions on the chest respectively move in directions of the two upper limbs by a preset distance, and the preset distance is a distance between a first center point determined when the first detection electrode is in contact with one upper limb of the human body, the second detection electrode is in contact with the other upper limb of the human body, and the third detection electrode is in contact with the lower limb of the human body and a second center point determined when the first detection electrode is in contact with one upper limb of the human body, and the second detection electrode is in contact with the other upper limb of the human body.

Based on the prompt, while the first detection electrode 30 is in contact with one upper limb (for example, the upper left limb) of the human body, and the second detection electrode 40 is in contact with the other upper limb (for example, the upper right limb) of the human body, the third detection electrode 50 is in contact with the first equivalent position R1, the second equivalent position R2, the third equivalent position R3, the fourth equivalent position R4, the fifth equivalent position R5, and the sixth equivalent position R6 in sequence, and the first detection electrode 30, the second detection electrode 40, and the third detection electrode 50 collect the potential signals of the surfaces of the respective corresponding limbs.

This is because vector directions in which the second center point determined when the first detection electrode is in contact with one upper limb of the human body, and the second detection electrode is in contact with the other upper limb of the human body points to the six equivalent positions on the chest are in a one-to-one correspondence with vector directions in which the first center point determined when the first detection electrode is in contact with one upper limb of the human body, the second detection electrode is in contact with the other upper limb of the human body, and the third detection electrode is in contact with the lower limb of the human body points to the six preset positions on the chest. Therefore, in this scenario, leads at the six equivalent positions on the chest may be considered as equivalent leads of leads at the six preset positions on the chest, so that detection of equivalent leads of chest leads V1, V2, V3, V4, V5, and V6 is implemented, to obtain electrocardiogram signals corresponding to the six chest leads.

S1404: Determine an electrocardiogram signal corresponding to a lead I based on a potential difference between a potential signal of a surface of the upper left limb and a potential signal of a surface of the upper right limb; determine an electrocardiogram signal corresponding to a lead II based on a potential difference between a potential signal of a surface of the lower limb and the potential signal of the surface of the upper right limb; determine an electrocardiogram signal corresponding to a lead III based on a potential difference between the potential signal of the surface of the lower limb and the potential signal of the surface of the upper left limb; and determine a potential of the first center point, and determine electrocardiogram signals corresponding leads aVR, aVL, and aVF based on a potential difference between the potential of the first center point and the potential signal of the surface of the upper left limb, a potential difference between the potential of the first center point and the potential signal of the surface of the upper right limb, and a potential difference between the potential of the first center point and the potential signal of the surface of the lower limb.

Specifically, an electrocardiogram signal processing module 60 collects potential signals on the detection electrodes. The electrocardiogram signal corresponding to the lead I is determined based on the potential difference between the potential signal of the surface of the upper left limb and the potential signal of the surface of the upper right limb, the electrocardiogram signal corresponding to the lead II may be determined based on the potential difference between the potential signal of the surface of the lower limb and the potential signal of the surface of the upper right limb, and the electrocardiogram signal corresponding to the lead III is determined based on the potential difference between the potential signal of the surface of the lower limb and the potential signal of the surface of the upper left limb. A potential of a Wilson center point (also referred to as the first center point T1) of the three electrodes may be positioned based on the potential signal of the surface of the upper left limb, the potential signal of the surface of the upper right limb, and the potential signal of the surface of the lower limb, and an electrocardiogram signal corresponding to a lead aVR, an electrocardiogram signal corresponding to a lead aVL, and an electrocardiogram signal corresponding to a lead aVF are determined based on the potential difference between the potential of the first center point T1 and the potential signal of the surface of the upper left limb, the potential difference between the potential of the first center point T1 and the potential signal of the surface of the upper right limb, and the potential difference between the potential of the first center point T1 and the potential signal of the surface of the lower limb, so that electrocardiogram signals corresponding to six limb leads can be obtained.

S1405: Determine a potential of the second center point, and determine a signal of a lead V1, a signal of a lead V2, a signal of a lead V3, a signal of a lead V4, a signal of a lead V5, and a signal of a lead V6 based on a potential difference between the potential of the second center point and a potential signal of a surface of each of the six equivalent positions on the chest of the human body, to obtain electrocardiogram signals corresponding to twelve leads. The potential of the second center point is a potential difference between a potential signal collected when the first detection electrode is in contact with one upper limb of the human body and a potential signal collected when the second detection electrode is in contact with the other upper limb of the human body.

S1406: Determine whether a twelve-lead ECG matches a preset twelve-lead ECG; if the twelve-lead ECG matches the preset twelve-lead ECG, execute step S1407; and if the twelve-lead ECG does not match the preset twelve-lead ECG, execute step S1408.

The health status reminding information is output when an electrocardiogram signal corresponding to at least one lead in the electrocardiogram signals corresponding to the twelve leads has a typical disease-related feature (such as ST segment elevation and a pathologic Q wave) compared with a normal electrocardiogram signal.

For example, the health status reminding information may be output when one of the electrocardiogram signals corresponding to the twelve leads does not match a corresponding preset electrocardiogram signal, for example, has the typical disease-related feature compared with the normal electrocardiogram signal, or the health status reminding information may be output when a plurality of electrocardiogram signals in the electrocardiogram signals corresponding to the twelve leads do not match corresponding preset electrocardiogram signals, for example, have the typical disease-related feature compared with the normal electrocardiogram signal, or the like.

S1407: Output information indicating a normal health status.

For example, a health status may be displayed through the display of the smartwatch 100. When the health status is normal, the user may be notified through, for example, a statement (which is played through a speaker).

S1408: Output the health status reminding information.

When the health status is abnormal, the user may be reminded through a statement (which is played through the speaker) and/or an alarm or the like, to improve user experience. The reminding information may alternatively be sent to a mobile phone of a family member through a wireless module, to notify a family member user of the health status.

In conclusion, twelve-lead ECG measurement may be implemented by using the three electrodes. Scenarios, such as acute myocardial infarction, that need to be detected by using the multi-lead ECG may be effectively detected in a timely manner, and a structure is simple.

To describe the beneficial effect in detail, descriptions are provided below by performing comparison with a related technology.

Figure 15:
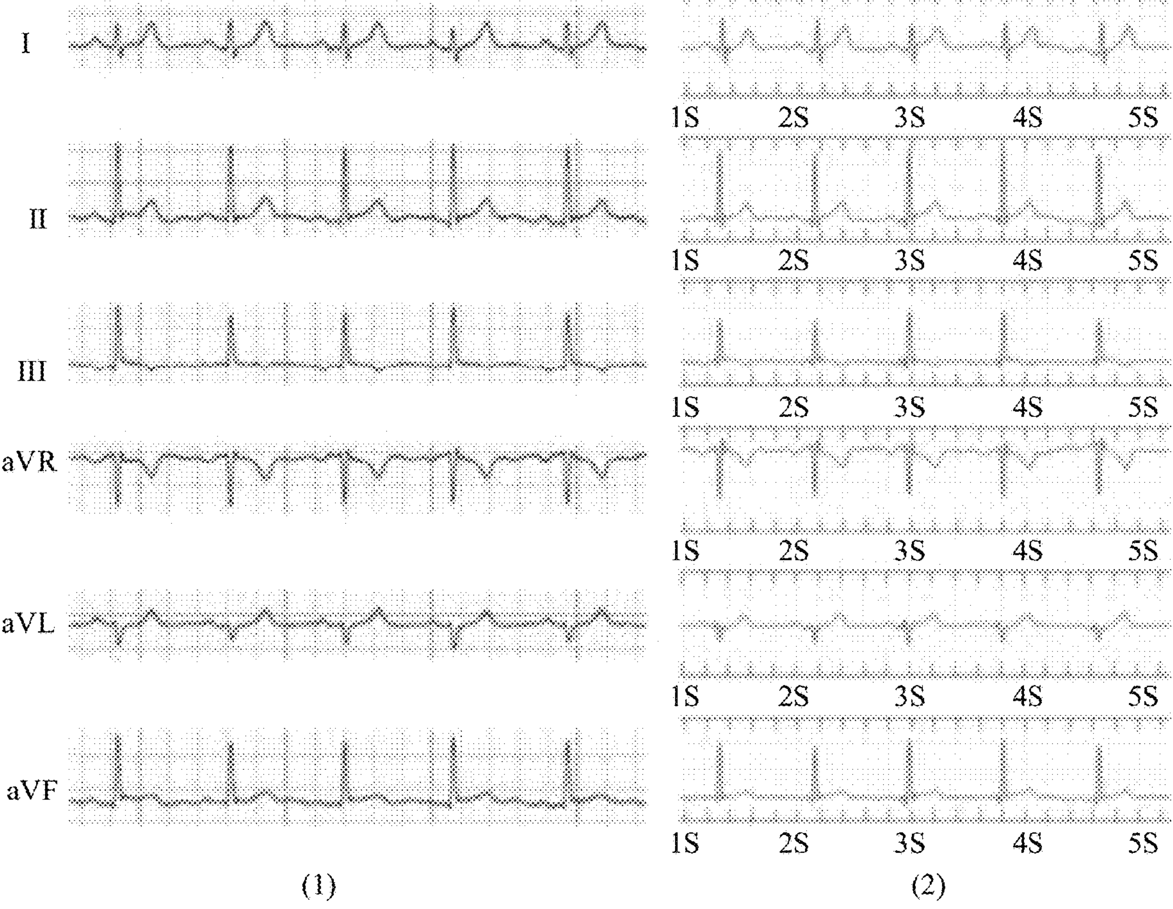
FIG. 15 is a comparison simulation diagram of a related technology and an embodiment of this application.
Figure 16:
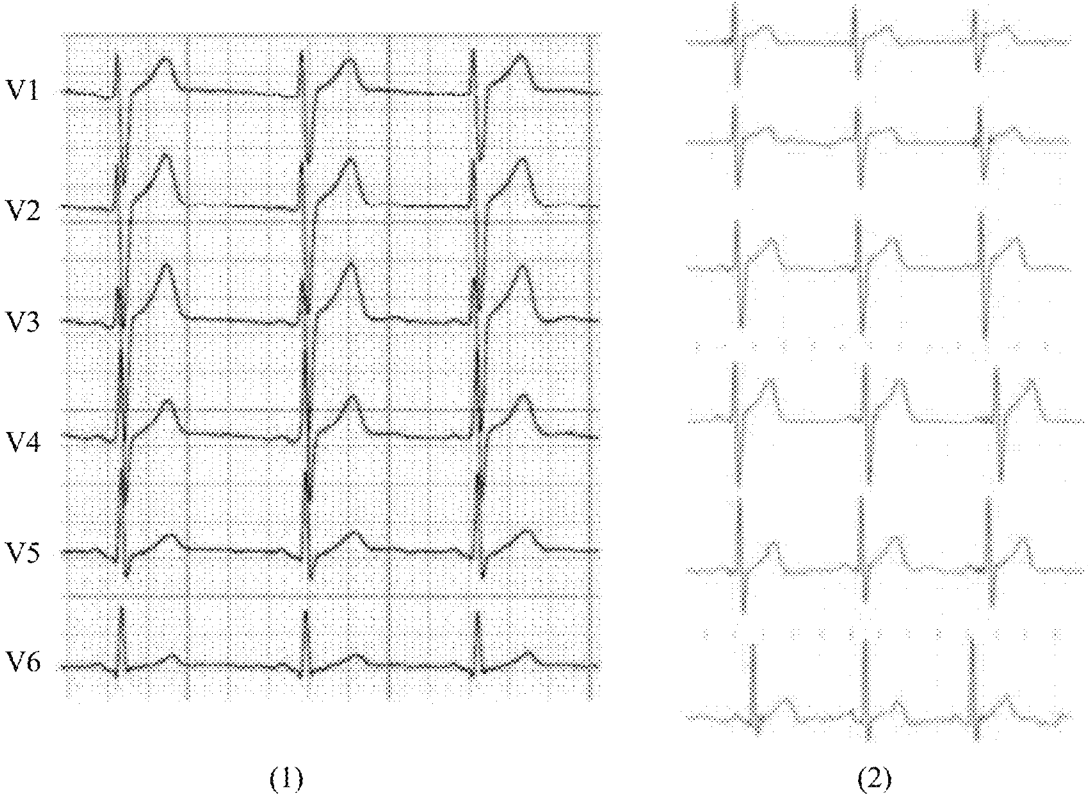
FIG. 16 is a comparison simulation diagram of a related technology and an embodiment of this application.

FIG. 15 and FIG. 16 both are comparison simulation diagrams of a related technology and an embodiment of this application. (1) in FIG. 15 is an electrocardiogram obtained by using the medical electrocardiograph equipment to detect the six limb leads in the related technology, and (2) in FIG. 15 is an electrocardiogram obtained by using the three electrodes to detect the six limb leads in this embodiment of this application. (1) in FIG. 16 is an electrocardiogram obtained by using the medical electrocardiograph equipment to detect the six chest leads in the related technology, and (2) in FIG. 16 is an electrocardiogram obtained by using the three electrodes to detect the six chest leads in this embodiment of this application.

Six simulation results in FIG. 15 are the electrocardiogram signal corresponding to the lead I, the electrocardiogram signal corresponding to the lead II, the electrocardiogram signal corresponding to the lead III, the electrocardiogram signal corresponding to the lead aVR, the electrocardiogram signal corresponding to the lead aVL, and the electrocardiogram signal corresponding to the lead aVF in sequence from top to bottom. Six simulation results in FIG. 16 are the electrocardiogram signal corresponding to the lead V1, the electrocardiogram signal corresponding to the lead V2, the electrocardiogram signal corresponding to the lead V3, the electrocardiogram signal corresponding to the lead V4, the electrocardiogram signal corresponding to the lead V5, and the electrocardiogram signal corresponding to the lead V6 in sequence from top to bottom.

It can be learned from FIG. 15 and FIG. 16 that a result of the electrocardiogram signals that correspond to the twelve leads and that are detected by using the smartwatch 100 and the multi-lead electrocardiogram detection method provided in this embodiment of this application is basically the same as a result of the electrocardiogram signals that correspond to the twelve leads and that are detected by using the medical electrocardiograph equipment. In other words, the smartwatch 100 and the multi-lead electrocardiogram detection method provided in this embodiment of this application and the medical electrocardiograph equipment have a same function.

Figure 17:
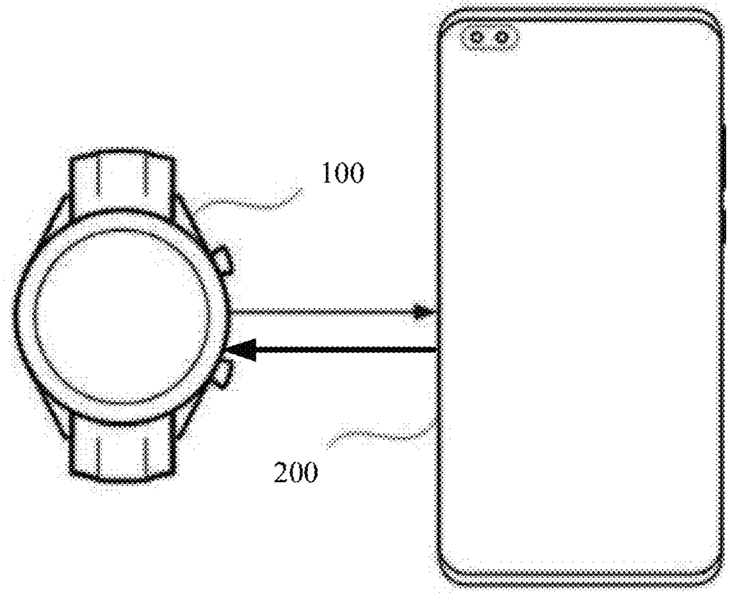
FIG. 17 is a diagram of a structure of a multi-lead electrocardiogram detection system according to an embodiment of this application.

This embodiment further provides a multi-lead electrocardiogram detection system. Refer to FIG. 17. The multi-lead electrocardiogram detection system provided in this embodiment of this application specifically includes: a smartwatch 100 and a mobile phone 200. A communication connection is pre-established between the smartwatch 100 and the mobile phone 200, for example, may be a Bluetooth communication connection and/or a wireless communication connection.

The smartwatch 100 may collect potential signals of surfaces of respective corresponding limbs, and send the potential signals to the mobile phone 200. The mobile phone 200 processes the potential signals to obtain a twelve-lead ECG, compares the twelve-lead ECG with a preset twelve-led ECG, and send reminding information to the smartwatch 100 when electrocardiogram signals corresponding to twelve leads do not match preset electrocardiogram signals corresponding to the twelve leads. The smartwatch 100 reminds a user based on the reminding information through a statement (which is played through a speaker) and/or an alarm or the like, to improve user experience. Alternatively, the mobile phone 200 may process the potential signals to obtain the twelve-lead ECG, and sends the twelve-lead ECG to the smartwatch 100. The smartwatch 100 compares the twelve-lead ECG with the preset twelve-led ECG, and reminds the user through the statement (which is played through the speaker) and/or the alarm or the like when the electrocardiogram signals corresponding to the twelve leads do not match the preset electrocardiogram signals corresponding to the twelve leads, to improve user experience. For detailed explanation and descriptions, refer to the foregoing embodiments. Details are not described herein again.

This embodiment further provides a computer storage medium. The computer storage medium stores computer instructions. When the computer instructions are run on an electronic device, the electronic device is enabled to perform the related method steps to implement the multi-lead electrocardiogram detection method in the foregoing embodiments.

This embodiment further provides a computer program product. When the computer program product is run on a computer, the computer is enabled to perform the foregoing related steps to implement the multi-lead electrocardiogram detection method in the foregoing embodiments.

In addition, an embodiment of this application further provides an apparatus. The apparatus may be specifically a chip, a component, or a module. The apparatus may include a processor and a memory that are connected. The memory is configured to store computer-executable instructions. When the apparatus runs, the processor may execute the computer-executable instructions stored in the memory, to enable the chip to perform the multi-lead electrocardiogram detection method in the foregoing method embodiments.

The electronic device (such as a smartwatch), the computer storage medium, the computer program product, and the chip that are provided in this embodiment are all configured to perform the corresponding method provided above. Therefore, for beneficial effect that can be achieved by the electronic device, the computer storage medium, the computer program product, and the chip, refer to the beneficial effect in the corresponding method provided above. Details are not described herein again.

Based on the descriptions of the foregoing implementations, a person skilled in the art may understand that for the purpose of convenient and brief description, division into the foregoing functional modules is merely used as an example for illustration. During actual application, the foregoing functions can be allocated to different functional modules for implementation according to a requirement, that is, an inner structure of an apparatus is divided into different functional modules to implement all or a part of the functions described above.

In the several embodiments provided in this application, it should be understood that the disclosed apparatus and method may be implemented in other manners. For example, the described apparatus embodiment is merely an example. For example, division into modules or units is merely logical function division and may be another division during actual implementation. For example, a plurality of units or components may be combined or integrated into another apparatus, or some features may be ignored or not performed. In addition, the displayed or discussed mutual couplings, direct couplings, or communication connections may be implemented through some interfaces. Indirect couplings or communication connections between apparatuses or units may be implemented in an electrical form, a mechanical form, or other forms.

In conclusion, the foregoing embodiments are merely intended for describing the technical solutions of this application, but not for limiting this application. Although this application is described in detail with reference to the foregoing embodiments, a person of ordinary skill in the art should understand that they may still make modifications to the technical solutions described in the foregoing embodiments or make equivalent replacements to some technical features thereof, without departing from the scope of the technical solutions of embodiments of this application.

The invention claimed is:

1. A method, comprising:

obtaining potential signals of surfaces of two upper limbs and a lower limb of a human body in response to a first operation, wherein the first operation is an operation that a first detection electrode is in contact with one upper limb of the human body, a second detection electrode is in contact with another upper limb of the human body, and a third detection electrode is in contact with a lower limb of the human body;

obtaining, in sequence, potential signals of surfaces of six equivalent positions on a chest of the human body in response to a second operation, wherein the second operation is an operation that the third detection electrode is in contact with the six equivalent positions on the chest of the human body in sequence, wherein the six equivalent positions on the chest are six positions obtained after six preset positions on the chest respectively move in directions of the two upper limbs by a preset distance, wherein the preset distance is a distance between a) a first center point when the first detection electrode is in contact with the one upper limb of the human body, the second detection electrode is in contact with the other upper limb of the human body, and the third detection electrode is in contact with the lower limb of the human body, and b) a second center point when the first detection electrode is in contact with the one upper limb of the human body, and the second detection electrode is in contact with the other upper limb of the human body; and generating electrocardiogram signals corresponding to twelve leads based on the potential signals of the surfaces of the two upper limbs and the lower limb of the human body and the potential signals of the surfaces of the six equivalent positions on the chest of the human body.

2. The method of claim 1, further comprising processing the obtained potential signals of the surfaces of the two upper limbs and the lower limb of the human body to determine electrocardiogram signals corresponding to six limb leads.

3. The method of claim 2, wherein the two upper limbs comprise an upper left limb and an upper right limb, and wherein the electrocardiogram signals corresponding to six limb leads comprise:

an electrocardiogram signal corresponding to a lead I based on a potential difference between a potential signal of a surface of the upper left limb and a potential signal of a surface of the upper right limb;

an electrocardiogram signal corresponding to a lead II based on a potential difference between a potential signal of a surface of the lower limb and the potential signal of the surface of the upper right limb;

an electrocardiogram signal corresponding to a lead III based on a potential difference between the potential signal of the surface of the lower limb and the potential signal of the surface of the upper left limb; and an electrocardiogram signal corresponding to a lead aVR, an electrocardiogram signal corresponding to a lead aVL, and an electrocardiogram signal corresponding to a lead aVF based on a potential difference between a potential of the first center point and the potential signal of the surface of the upper left limb, a potential difference between the potential of the first center point and the potential signal of the surface of the upper right limb, and a potential difference between the potential of the first center point and the potential signal of the surface of the lower limb.

4. The method of claim 1, further comprising processing the obtained potential signals of the surfaces of the two upper limbs of the human body and the six equivalent positions on the chest of the human body to obtain electrocardiogram signals corresponding to six chest leads.

5. The method of claim 4, wherein the electrocardiogram signals corresponding to six chest leads comprise an electrocardiogram signal corresponding to a lead V1, an electrocardiogram signal corresponding to a lead V2, an electrocardiogram signal corresponding to a lead V3, an electrocardiogram signal corresponding to a lead V4, an electrocardiogram signal corresponding to a lead V5, and an electrocardiogram signal corresponding to a lead V6 based on a potential difference between a potential of the second center point and a potential signal of a surface of each of the six equivalent positions on the chest of the human body.

6. The method of claim 1, wherein before the obtaining, in sequence, potential signals of surfaces of six equivalent positions on the chest of the human body in response to a second operation, the method further comprises displaying a first interface that comprises a first information prompt box, wherein the first information prompt box to prompts the six equivalent positions on the chest.

7. The method of claim 6, wherein before the obtaining, in sequence, potential signals of surfaces of six equivalent positions on the chest of the human body in response to a second operation, the method further comprises obtaining a preview image of an upper body of the human body that is captured by a camera, wherein a sequence of target objects in the preview image comprise the six equivalent positions on the chest of the human body.

8. The method of claim 1, further comprising providing health status reminding information when the electrocardiogram signals corresponding to the twelve leads do not match preset electrocardiogram signals corresponding to the twelve leads.

9. The method of claim 1, wherein the six preset positions comprise:

a first preset position that is a fourth intercostal space right of a sternum of the human body;

a second preset position that is a fourth intercostal space left of the sternum;

a third preset position;

a fourth preset position, wherein the third preset position is located at a midpoint of a connection line between the second preset position and the fourth preset position, wherein the fourth preset position is an intersection of a left midclavicular line and a fifth intercostal space;

a fifth preset position that is a position that is on a left anterior axillary line and that is at a same horizontal level as the fourth preset position; and a sixth preset position that is a position that is on the left midclavicular line and that is at the same horizontal level as the fourth preset position.

10. The method of claim 9, further comprising processing the obtained potential signals of the surfaces of the two upper limbs and the lower limb of the human body to generate electrocardiogram signals corresponding to six limb leads.

11. The method of claim 10, wherein the two upper limbs comprise an upper left limb and an upper right limb, and wherein the electrocardiogram signals corresponding to six limb leads comprise:

an electrocardiogram signal corresponding to a lead I based on a potential difference between a potential signal of a surface of the upper left limb and a potential signal of a surface of the upper right limb;

an electrocardiogram signal corresponding to a lead II based on a potential difference between a potential signal of a surface of the lower limb and the potential signal of the surface of the upper right limb;

an electrocardiogram signal corresponding to a lead III based on a potential difference between the potential signal of the surface of the lower limb and the potential signal of the surface of the upper left limb; and an electrocardiogram signal corresponding to a lead aVR, an electrocardiogram signal corresponding to a lead aVL, and an electrocardiogram signal corresponding to a lead aVF based on a potential difference between a potential of a Wilson center point and the potential signal of the surface of the upper left limb, a potential difference between the potential of the Wilson center point and the potential signal of the surface of the upper right limb, and a potential difference between the potential of the Wilson center point and the potential signal of the surface of the lower limb.

12. The method of claim 9, further comprising processing the obtained potential signals of the surfaces of the two upper limbs of the human body and the six equivalent positions on the chest of the human body to obtain electrocardiogram signals corresponding to six chest leads.

13. The method of claim 12, wherein the electrocardiogram signals corresponding to six chest leads comprise an electrocardiogram signal corresponding to a lead V1, an electrocardiogram signal corresponding to a lead V2, an electrocardiogram signal corresponding to a lead V3, an electrocardiogram signal corresponding to a lead V4, an electrocardiogram signal corresponding to a lead V5, and an electrocardiogram signal corresponding to a lead V6 based on a potential difference between a potential of the second center point and a potential signal of a surface of each of the six equivalent positions on the chest of the human body.

14. The method of claim 9, wherein before the obtaining, in sequence, potential signals of surfaces of six equivalent positions on the chest of the human body in response to a second operation, the method further comprises displaying a first interface that comprises a first information prompt box, wherein the first information prompt box prompts the six equivalent positions on the chest.

15. The method of claim 14, wherein before the obtaining, in sequence, potential signals of surfaces of six equivalent positions on the chest of the human body in response to a second operation, the method further comprises obtaining a preview image of an upper body of the human body that is captured by a camera, wherein a sequence of target objects in the preview image comprise the six equivalent positions on the chest of the human body.

16. The method of claim 9, further comprising providing health status reminding information when the electrocardiogram signals corresponding to the twelve leads do not match preset electrocardiogram signals corresponding to the twelve leads.

17. An electronic device, comprising:

a first detection electrode;

a second detection electrode;

a third detection electrode, wherein the first, second, and third detection electrodes are configured to collect electrical signals on a surface of a human body;

one or more processors coupled to the first, second, and third detection electrodes; and a memory coupled to the one or more processors and configured to store instructions that, when executed by the one or more processors, cause the electronic device to be configured to:

obtain potential signals of surfaces of two upper limbs and a lower limb of the human body in response to a first operation, wherein the first operation is an operation that the first detection electrode is in contact with one upper limb of the human body, the second detection electrode is in contact with another upper limb of the human body, and the third detection electrode is in contact with a lower limb of the human body;

obtain, in sequence, potential signals of surfaces of six equivalent positions on a chest of the human body in response to a second operation, wherein the second operation is an operation that the third detection electrode is in contact with the six equivalent positions on the chest of the human body in sequence, wherein the six equivalent positions on the chest are six positions obtained after six preset positions on the chest respectively move in directions of the two upper limbs by a preset distance, wherein the preset distance is a distance between a) a first center point when the first detection electrode is in contact with the one upper limb of the human body, the second detection electrode is in contact with the other upper limb of the human body, and the third detection electrode is in contact with the lower limb of the human body, and b) a second center point when the first detection electrode is in contact with the one upper limb of the human body, and the second detection electrode is in contact with the other upper limb of the human body; and generate electrocardiogram signals corresponding to twelve leads based on the potential signals of the surfaces of the two upper limbs and the lower limb of the human body and the potential signals of the surfaces of the six equivalent positions on the chest of the human body.

18. The electronic device of claim 17, further comprising a display configured to display the electrocardiogram signals corresponding to twelve leads.

19. The electronic device of claim 17, wherein the six preset positions comprise:

a first preset position that is a fourth intercostal space right of a sternum of the human body;

a second preset position that is a fourth intercostal space left of the sternum;

a third preset position;

a fourth preset position, wherein the third preset position is located at a midpoint of a connection line between the second preset position and the fourth preset position, wherein the fourth preset position is an intersection of a left midclavicular line and a fifth intercostal space;

a fifth preset position that is a position that is on a left anterior axillary line and that is at a same horizontal level as the fourth preset position; and a sixth preset position that is a position that is on the left midclavicular line and that is at the same horizontal level as the fourth preset position.

20. A multi-lead electrocardiogram detection system, comprising:

a smart wearable device comprising a first detection electrode, a second detection electrode, and a third detection electrode, wherein the first, second, and third detection electrodes are configured to collect electrical signals on a surface of a human body;

a mobile phone;

one or more processors; and a memory coupled to the one or more processors and configured to store instructions that, when executed by the one or more processors, cause the system to be configured to;

obtain potential signals of surfaces of two upper limbs and a lower limb of a human body in response to a first operation, wherein the first operation is an operation that the first detection electrode is in contact with one upper limb of the human body, the second detection electrode is in contact with another upper limb of the human body, and the third detection electrode is in contact with a lower limb of the human body;

obtain, in sequence, potential signals of surfaces of six equivalent positions on a chest of the human body in response to a second operation, wherein the second operation is an operation that the third detection electrode is in contact with the six equivalent positions on the chest of the human body in sequence, wherein the six equivalent positions on the chest are six positions obtained after six preset positions on the chest respectively move in directions of the two upper limbs by a preset distance, wherein the preset distance is a distance between a) a first center point when the first detection electrode is in contact with the one upper limb of the human body, the second detection electrode is in contact with the other upper limb of the human body, and the third detection electrode is in contact with the lower limb of the human body, and b) a second center point when the first detection electrode is in contact with the one upper limb of the human body, and the second detection electrode is in contact with the other upper limb of the human body; and generate electrocardiogram signals corresponding to twelve leads based on the potential signals of the surfaces of the two upper limbs and the lower limb of the human body and the potential signals of the surfaces of the six equivalent positions on the chest of the human body.

* * * * *